United States Patent
Kim et al.

(10) Patent No.: US 9,631,011 B2
(45) Date of Patent: Apr. 25, 2017

(54) GREMLIN-1 ANTIBODY

(71) Applicants: SNU R&DB Foundation, Seoul (KR); Hyun Kee Kim, Seoul (KR)

(72) Inventors: Hyun Kee Kim, Seoul (KR); Junho Chung, Gyeonggi-do (KR); Min Soo Kim, Gyeonggi-do (KR); Soo Min Yoon, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/385,483

(22) PCT Filed: Mar. 15, 2013

(86) PCT No.: PCT/KR2013/002119
§ 371 (c)(1),
(2) Date: Sep. 15, 2014

(87) PCT Pub. No.: WO2013/137686
PCT Pub. Date: Sep. 19, 2013

(65) Prior Publication Data
US 2015/0158938 A1 Jun. 11, 2015

Related U.S. Application Data

(60) Provisional application No. 61/611,285, filed on Mar. 15, 2012.

(51) Int. Cl.
*C07K 16/18* (2006.01)
*C07K 16/28* (2006.01)

(52) U.S. Cl.
CPC .......... *C07K 16/18* (2013.01); *C07K 16/2863* (2013.01); *C07K 2317/21* (2013.01); *C07K 2317/24* (2013.01); *C07K 2317/565* (2013.01); *C07K 2317/622* (2013.01); *C07K 2317/70* (2013.01); *C07K 2317/73* (2013.01); *C07K 2317/76* (2013.01)

(58) Field of Classification Search
CPC ............ C07K 16/2863; C07K 2317/24; C07K 2317/565
USPC .................. 424/133.1; 530/387.3, 389.1
See application file for complete search history.

(56) References Cited

U.S. PATENT DOCUMENTS

| | | | |
|---|---|---|---|
| 7,408,043 B2 | 8/2008 | Chung et al. | 530/387.1 |
| 7,655,417 B2 | 2/2010 | Chung et al. | 435/455 |
| 7,718,174 B2 | 5/2010 | Chung et al. | 424/133.1 |
| 7,744,873 B2 | 6/2010 | Clark et al. | 424/130.1 |
| 8,008,448 B2 | 8/2011 | Park et al. | 530/388.1 |
| 8,586,033 B2 | 11/2013 | Barbas et al. | 424/130.1 |
| 2007/0036789 A1 | 2/2007 | Chung | 424/145.1 |
| 2007/0280941 A1 | 12/2007 | Chung et al. | 424/143.1 |
| 2008/0038256 A1 | 2/2008 | Chung et al. | 424/133.1 |
| 2008/0051361 A1 | 2/2008 | Chatterton et al. | 514/44 |
| 2008/0213763 A1 | 9/2008 | Kim et al. | 435/6.11 |
| 2008/0213764 A1 | 9/2008 | Kim et al. | 435/6.11 |
| 2009/0023894 A1 | 1/2009 | Chung et al. | 530/32.7 |
| 2009/0041757 A1 | 2/2009 | Zhen et al. | 424/130.1 |
| 2009/0123918 A1 | 5/2009 | Kim et al. | 435/6.11 |
| 2009/0221794 A1 | 9/2009 | Kim et al. | 530/350 |
| 2010/0172902 A1 | 7/2010 | Chung et al. | 424/133.1 |
| 2010/0205681 A1 | 8/2010 | Kim et al. | 800/15 |
| 2010/0297101 A1 | 11/2010 | Barbas et al. | 424/130.1 |
| 2011/0319297 A1 | 12/2011 | Khvorova et al. | 506/16 |
| 2014/0056926 A1 | 2/2014 | Chung et al. | 424/181.1 |
| 2016/0024195 A1* | 1/2016 | Economides | C07K 16/24 424/134.1 |

FOREIGN PATENT DOCUMENTS

WO WO 2005/029082 3/2005
WO WO 2007/124486 11/2007

OTHER PUBLICATIONS

Sha et al. (Fertil Steril. Feb. 2009;91(2):350-8. doi: 10.1016/j.fertnstert.2007.12.007. Epub Mar. 7, 2008).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Church et al. (Biochem. J. (2015) 466, 55-68).*
Letter/Written Disclosure of the Information Disclosure Statement for the above-referenced application, mailed on Dec. 5, 2014, 2 pages.
Bobinac et al., "Expression of bone morphogenetic proteins in human metastatic prostate and breast cancer," Croat Med. J 46:389-396 (2005).
Chen et al., "Bone morphogenetic proteins," Growth Factors 22:233-241 (2004).
Chen et al., "Cutting edge: bone morphogenetic protein antagonists Drm/Gremlin and Dan interact with Slits and act as negative regulators of monocyte chemotaxis," J Immunol 173:5914-5917 (2004).
Chung et al., "Integrin alphaIIbbeta3-specifc synthetic human monoclonal antibodies and HCDR3 peptides that potently inhibit platelet aggregation," FASEB J 18:361-363 (2004).
Gupta, G. and J. Massague, "Cancer metastasis:building a framework," Cell 127:679-695 (2006).
Kim et al., "A neutralizable epitope is induced on HGF upon its interaction with its receptor cMet," Biochem Biophys Res Commun 354:115-121 (2007).

(Continued)

*Primary Examiner* — Lynn Bristol
(74) *Attorney, Agent, or Firm* — Lex IP Meister, PLLC

(57) ABSTRACT

The present invention relates to a Gremlin-1 antibody that inhibits Gremlin-1 in a manner independent of bone morphogenetic protein (BMP) or vascular endothelial growth factor receptor-2 (VEGFR-2), thus providing the effect of treating cancer. The antibody of the present invention inhibits cell migration, cell invasion and cell proliferation which are dependent on Gremlin-1, and therefore, can be effectively used in treating cancer or immune disease.

5 Claims, 14 Drawing Sheets

(56) References Cited

OTHER PUBLICATIONS

Kim et al., "Gremlin-1 induces BMP-independent tumor cell proliferation, migration, and invasion," PLoS One. 7(4):e35100, 8 pages (2012).
Koli et al., "Bone morphogenetic protein-4 inhibitor gremlin is overexpressed in idiopathic pulmonary fibrosis," Am J Pathol 169:61-71 (2006).
Lappin et al., "Gremlins, glomeruli and diabetic nephropathy," Curr Opin Nephrol Hypertens 9:469-472 (2000).
Lee et al., "Production and characterization of monoclonal antibody to botulinum neurotoxin type B light chain by phage display," Hybridoma (Larchmt) 27:18-24 (2008).
Li et al., "Panaxadiol, a purified ginseng component, enhances the anti-cancer effects of 5-fluorouracil in human colorectal cancer cells," Cancer Chemother Pharmacol 64:1097-1104 (2009).
Lu et al., "The bone morphogenic protein antagonist gremlin regulates proximal-distal patterning of the lung," Dev Dyn 222:667-680 (2001).
Merino et al., "The BMP antagonist Gremlin regulates outgrowth, chondrogenesis and programmed cell death in the developing limb," Development 126:5515-5522 (1999).
Mezzano et al. "Expression of gremlin, a bone morphogenetic protein antagonist, in glomerular crescents of pauci-immune glomerulonephritis," Nephrol Dial Transplant. 22(7):1882-1890 (2007).
Mitola et al., "Gremlin is a novel agonist of the major proangiogenic receptor VEGFR2," Blood 116:3677-3680 (2010).
Namkoong et al., "The bone morphogenetic protein antagonist gremlin 1 is overexpressed in human cancers and interacts with YWHAH protein," BMC Cancer 6:74, 13 pages (2006).
Park et al., "A sensitive enzyme immunoassay for measuring cotinine in passive smokers," Clin Chim Acta 411:1238-1242 (2010).
Pereira et al., "Bone morphogenetic proteins induce gremlin, a protein that limits their activity in osteoblasts," Endocrinology. 141(12):4558-4563 (2000).
Perl et al., "A causal role for E-cadherin in the transition from adenoma to carcinoma," Nature 392:190-193 (1998).
Rosso et al., "The ALCAM shedding by the metalloprotease ADAM17/TACE is involved in motility of ovarian carcinoma cells," Mol Cancer Res 5:1246-1253 (2007).
Sha et al., "Elevated levels of gremlin-1 in eutopic endometrium and peripheral serum in patients with endometriosis," Fertil Steril 91:350-358 (2009).
Shi et al., "Gremlin negatively modulates BMP-4 induction of embryonic mouse lung branching morphogenesis," Am J Physiol Lung Cell Mol Physiol 280:L1030-L1039 (2001).
Singh A. and R. Morris, "The Yin and Yang of bone morphogenetic proteins in cancer," Cytokine Growth Factor Rev 21:299-313 (2010).
Sneddon et al., "Bone morphogenetic protein antagonist gremlin 1 is widely expressed by cancer-associated stromal cells and can promote tumor cell proliferation," Proc Natl Acad Sci U S A 103:14842-14847 (2006).
Stanley et al., "DAN is a secreted glycoprotein related to Xenopus cerberus," Mech Dev 77:173-184 (1998).
Sun et al., "BMP4 activation and secretion are negatively regulated by an intracellular gremlin-BMP4 interaction," J Biol Chem 281:29349-29356 (2006).
Tomayko M. and C. Reynolds, "Determination of subcutaneous tumor size in athymic (nude) mice," Cancer Chemother Pharmacol 24:148-154 (1989).
Topol et al., "Biosynthesis, post-translation modification, and functional characterization of Drm/Gremlin," J Biol Chem 275:8785-8793 (2000).
Topol et al., "DRM/GREMLIN (CKTSF1B1) maps to human chromosome 15 and is highly expressed in adult and fetal brain," Cytogenet Cell Genet 89:79-84 (2000).
Topol et al., "Identification of drm, a novel gene whose expression is suppressed in transformed cells and which can inhibit growth of normal but not transformed cells in culture," Mol Cell Biol 17:4801-4810 (1997).
International Search Report and Written Opinion, issued Jun. 25, 2013, in connection with International Patent Application No. PCT/KR2013/002119 [English Translation] 13 pages.
International Preliminary Report on Patentability, issued Sep. 16, 2014, in connection with International Patent Application No. PCT/KR2013/002119 [English Translation] 8 pages.
Letter/Written Disclosure of the Information Disclosure Statement for the above-referenced application, mailed Jan. 13, 2016, 2 pages.
Stabile et al., "Bone morphogenic protein antagonist Drm/gremlin is a novel proangiogenic factor." Blood. 109(5):1834-1840 (2007).
Examination Report, issued Oct. 16, 2015, in connection with Australian Patent Application No. 2013232855, 5 pages.
Extended European Search Report, issued Oct. 23, 2015, in connection with European Patent Application No. 13 760 897.2, 8 pages.
Office Action, issued Oct. 27, 2015, in connection with Japanese Patent Application No. 2015/500366, 28 pages [English translation and original document in Japanese].

* cited by examiner

SEQUENCE LISTING

<160> NUMBER OF SEQ ID NOS: 40

<210> SEQ ID NO 1
<211> LENGTH: 110
<212> TYPE: PRT
<213> ORGANISM: Artificial Sequence
<220> FEATURE:
<223> OTHER INFORMATION: light chain variable region of R-80 antibody

<400> SEQUENCE: 1

```
Glu Leu Val Leu Thr Gln Ser Pro Ser Val Gln Val Asn Leu Gly Gln
 1               5                  10                  15

Thr Val Ser Leu Thr Cys Thr Ala Asp Thr Leu Ser Arg Ser Tyr Ala
            20                  25                  30

Ser Trp Tyr Gln Gln Lys Pro Gly Gln Ala Pro Val Leu Leu Ile Tyr
        35                  40                  45

Arg Asp Thr Ser Arg Pro Ser Gly Val Pro Asp Arg Phe Ser Gly Ser
    50                  55                  60

Ser Ser Gly Asn Thr Ala Thr Leu Thr Ile Ser Gly Ala Gln Ala Gly
65                  70                  75                  80

Asp Glu Ala Asp Tyr Tyr Cys Ala Thr Ser Asp Gly Ser Gly Ser Ser
                85                  90                  95

Tyr Gln Phe Val Phe Gly Gly Gly Thr Gln Leu Thr Val Thr
            100                 105                 110
```

<210> SEQ ID NO 2
<211> LENGTH: 116
<212> TYPE: PRT
<213> ORGANISM: Artificial Sequence
<220> FEATURE:
<223> OTHER INFORMATION: heavy chain variable region of R-80 antibody

<400> SEQUENCE: 2

```
Lys Ser Val Glu Glu Ser Gly Gly Arg Leu Val Thr Pro Gly Thr Pro
 1               5                  10                  15

Leu Thr Leu Thr Cys Thr Val Ser Gly Phe Ser Leu Ser Arg Tyr Ala
            20                  25                  30

Met Gly Trp Val Arg Gln Ala Pro Gly Lys Gly Leu Glu Tyr Ile Gly
        35                  40                  45

Ile Ile Asn Pro Asn Thr Gly Ala Tyr Tyr Ala Ser Trp Ala Lys Gly
    50                  55                  60

Arg Phe Thr Ile Ser Lys Thr Ser Ser Thr Thr Val Asp Leu Lys Ile
65                  70                  75                  80

Thr Ser Pro Thr Thr Glu Asp Thr Ala Thr Tyr Phe Cys Ala Arg Tyr
                85                  90                  95

Ala Gly Gly Asn Arg Val Phe Lys Leu Trp Gly Pro Gly Thr Leu Val
            100                 105                 110

Thr Val Ser Ser
        115
```

<210> SEQ ID NO 3
<211> LENGTH: 110
<212> TYPE: PRT
<213> ORGANISM: Artificial Sequence
<220> FEATURE:
<223> OTHER INFORMATION: light chain variable region of R-88 antibody

<400> SEQUENCE: 3

```
Glu Leu Val Leu Thr Gln Ser Pro Ser Val Gln Val Asn Leu Gly Gln
 1               5                  10                  15
```

```
Thr Val Ser Leu Thr Cys Thr Ala Asp Thr Leu Ser Arg Arg Tyr Ala
            20                  25                  30

Ser Trp Tyr Gln Gln Lys Pro Gly Gln Ala Pro Val Leu Leu Ile Tyr
            35                  40                  45

Arg Asp Thr Ser Arg Pro Ser Gly Val Pro Asp Arg Phe Ser Gly Ser
50                      55                  60

Ser Ser Gly Asn Thr Ala Thr Leu Thr Ile Ser Gly Ala Gln Ala Gly
65                  70                  75                  80

Asp Glu Ala Asp Tyr Tyr Cys Ala Thr Ser Asp Gly Ser Gly Ser Ser
                85                  90                  95

Tyr Gln Phe Val Phe Gly Gly Thr Gln Leu Thr Val Thr
            100                 105                 110

<210> SEQ ID NO 4
<211> LENGTH: 120
<212> TYPE: PRT
<213> ORGANISM: Artificial Sequence
<220> FEATURE:
<223> OTHER INFORMATION: heavy chain variable region of R-88 antibody

<400> SEQUENCE: 4

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ser Trp Val Arg Gln Ala Pro Gly Lys Gly Leu Glu Trp Ile Gly
            35                  40                  45

Leu Ile Ser Ser Gly Ser Ala Tyr Tyr Ala Ser Trp Ala Lys Gly
    50                  55                  60

Arg Phe Thr Ile Ser Asn Pro Ser Ser Thr Val Asp Leu Lys Ile
65                  70                  75                  80

Thr Ser Pro Thr Thr Glu Asp Thr Ala Thr Tyr Phe Cys Ala Arg Tyr
                85                  90                  95

Leu Tyr Glu Ser Asp Gly Tyr Val Asn Ala Leu Asp Leu Trp Gly Pro
            100                 105                 110

Gly Thr Leu Val Thr Val Ser Ser
            115                 120

<210> SEQ ID NO 5
<211> LENGTH: 110
<212> TYPE: PRT
<213> ORGANISM: Artificial Sequence
<220> FEATURE:
<223> OTHER INFORMATION: light chain variable region of O-1 antibody

<400> SEQUENCE: 5

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30

Ser Val Thr Trp Tyr Gln Gln Leu Pro Gly Thr Ala Pro Lys Leu Leu
            35                  40                  45

Ile Tyr Asp Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Asp Ser Leu
```

Ser Gly Tyr Val Phe Gly Gly Gly Thr Lys Leu Thr Val Leu
                100                 105                 110

<210> SEQ ID NO 6
<211> LENGTH: 121
<212> TYPE: PRT
<213> ORGANISM: Artificial Sequence
<220> FEATURE:
<223> OTHER INFORMATION: heavy chain variable region of O-1 antibody

<400> SEQUENCE: 6

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Met Trp Asn Glu Val Ser Ala Phe Asp Tyr Trp Gly
            100                 105                 110

Gln Gly Thr Leu Val Thr Val Ser Ser
        115                 120

<210> SEQ ID NO 7
<211> LENGTH: 110
<212> TYPE: PRT
<213> ORGANISM: Artificial Sequence
<220> FEATURE:
<223> OTHER INFORMATION: light chain variable region of O-13 antibody

<400> SEQUENCE: 7

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Asp Val Asn Trp Tyr Gln Gln Leu Pro Gly Thr Ala Pro Lys Leu Leu
        35                  40                  45

Ile Tyr Tyr Asp Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Ala Tyr Val Phe Gly Gly Gly Thr Lys Leu Thr Val Leu
            100                 105                 110

<210> SEQ ID NO 8
<211> LENGTH: 121
<212> TYPE: PRT
<213> ORGANISM: Artificial Sequence
<220> FEATURE:
<223> OTHER INFORMATION: heavy chain variable region of O-13 antibody

<400> SEQUENCE: 8

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met Ser Trp Val Arg Gln Ala Pro Gly Lys Gly Leu Glu Trp Val
         35                  40                  45

Ser Ala Ile Ser Tyr Asp Asn Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Tyr His Asn Glu Ile Ala Pro Phe Asp Tyr Trp Gly
            100                 105                 110

Gln Gly Thr Leu Val Thr Val Ser Ser
            115                 120
```

<210> SEQ ID NO 9
<211> LENGTH: 110
<212> TYPE: PRT
<213> ORGANISM: Artificial Sequence
<220> FEATURE:
<223> OTHER INFORMATION: light chain variable region of O-26 antibody

<400> SEQUENCE: 9

```
Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Ser Asn
             20                  25                  30

Asp Val Thr Trp Tyr Gln Gln Leu Pro Gly Thr Ala Pro Lys Leu Leu
         35                  40                  45

Ile Tyr Ser Asp Ser His Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Tyr Val Phe Gly Gly Gly Thr Lys Leu Thr Val Leu
            100                 105                 110
```

<210> SEQ ID NO 10
<211> LENGTH: 121
<212> TYPE: PRT
<213> ORGANISM: Artificial Sequence
<220> FEATURE:
<223> OTHER INFORMATION: heavy chain variable region of O-26 antibody

<400> SEQUENCE: 10

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met Ser Trp Val Arg Gln Ala Pro Gly Lys Gly Leu Glu Trp Val
         35                  40                  45

Ser Ala Ile Ser Tyr Asp Asn Gly Asn Thr Tyr Tyr Ala Asp Ser Val
     50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                        85                  90                  95

Ala Lys Asp Gly Leu Glu Asn Glu Thr Ala Gly Phe Asp Tyr Trp Gly
            100                 105                 110

Gln Gly Thr Leu Val Thr Val Ser Ser
        115                 120

<210> SEQ ID NO 11
<211> LENGTH: 107
<212> TYPE: PRT
<213> ORGANISM: Artificial Sequence
<220> FEATURE:
<223> OTHER INFORMATION: light chain variable region of J-1 antibody

<400> SEQUENCE: 11

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 12
<211> LENGTH: 121
<212> TYPE: PRT
<213> ORGANISM: Artificial Sequence
<220> FEATURE:
<223> OTHER INFORMATION: heavy chain variable region of J-1 antibody

<400> SEQUENCE: 12

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ser Arg Gly Val Gly Lys Ser Arg His Gln Arg Phe Asp Tyr Trp Gly
            100                 105                 110

Gln Gly Thr Leu Val Thr Val Ser Ser
        115                 120

<210> SEQ ID NO 13
<211> LENGTH: 111
```

```
<212> TYPE: PRT
<213> ORGANISM: Artificial Sequence
<220> FEATURE:
<223> OTHER INFORMATION: light chain variable region of O-13 (humanized)
      antibody

<400> SEQUENCE: 13

Asp Ile Gln Met Thr Gln Ser Pro Ser Ser Leu Ser Ala Ser Val Gly
 1               5                  10                  15

Asp Arg Val Thr Ile Thr Cys Ser Gly Ser Ser Ser Asn Ile Gly Ser
            20                  25                  30

Asn Asp Val Asn Trp Tyr Gln Gln Lys Pro Gly Lys Ala Pro Lys Leu
        35                  40                  45

Leu Ile Tyr Tyr Asp Ser Lys Arg Pro Ser Gly Val Pro Ser Arg Phe
    50                  55                  60

Ser Gly Ser Arg Ser Gly Thr Asp Phe Thr Leu Thr Ile Ser Ser Leu
65                  70                  75                  80

Gln Pro Glu Asp Phe Ala Thr Tyr Tyr Cys Ala Thr Trp Asp Asp Ser
                85                  90                  95

Leu Ser Ala Tyr Val Phe Gly Gln Gly Thr Lys Val Glu Ile Lys
            100                 105                 110

<210> SEQ ID NO 14
<211> LENGTH: 121
<212> TYPE: PRT
<213> ORGANISM: Artificial Sequence
<220> FEATURE:
<223> OTHER INFORMATION: heavy chain variable region of O-13 (humanized)
      antibody

<400> SEQUENCE: 14

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ala Ala Ile Ser Tyr Asp Asn Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Asp Gly Tyr His Asn Glu Ile Ala Pro Phe Asp Tyr Trp Gly
            100                 105                 110

Gln Gly Thr Leu Val Thr Val Ser Ser
        115                 120

<210> SEQ ID NO 15
<211> LENGTH: 330
<212> TYPE: DNA
<213> ORGANISM: Artificial Sequence
<220> FEATURE:
<223> OTHER INFORMATION: light chain variable region of R-80 antibody

<400> SEQUENCE: 15
gagctcgtgc tgactcagtc gccctcagtg caggtgaact tgggacagac ggtctccctc      60
acatgcactg cagatacact gagcagaagt tatgcttcct ggtaccagca gaagccaggc     120 caggccctg tgctgctcat ctacagggat accagtcggc cctcaggggt ccctgaccgg     180
```

```
ttctctggct ccagctcagg aacacggcc accctgacca tcagtggggc ccaggctggg    240
gacgaggctg actactattg tgctacaagc gatggcagtg cagcagcta tcagtttgtg    300 ttcggcggag ggacccagct gaccgtcaca                                    330
```

<210> SEQ ID NO 16
<211> LENGTH: 348
<212> TYPE: DNA
<213> ORGANISM: Artificial Sequence
<220> FEATURE:
<223> OTHER INFORMATION: heavy chain variable region of R-80 antibody

<400> SEQUENCE: 16

```
aagtcggtgg aggagtccgg gggtcgcctg gtcacgcctg gacacccct gacactcacc    60 tgcacagtct ctggattctc cctcagtagg tatgcaatgg gctgggtccg ccaggctcca    120
gggaaggggc tggaatacat cggaatcatt aatcctaata ctggcgcata ctacgcgagc    180
tgggcaaaag gccgattcac catctccaaa acctcgtcga ccacggtgga tctgaaaatc    240
accagtccga caaccgaaga cacggccacc tatttctgcg ccagatatgc tggtggtaat    300
cgggttttta aattgtgggg cccaggcacc ctggtcaccg tctcctca               348
```

<210> SEQ ID NO 17
<211> LENGTH: 330
<212> TYPE: DNA
<213> ORGANISM: Artificial Sequence
<220> FEATURE:
<223> OTHER INFORMATION: light chain variable region of R-88 antibody

<400> SEQUENCE: 17

```
gagctcgtgc tgactcagtc gccctcagtg caggtgaact tgggacagac ggtctccctc    60
acatgcactg cagatacact gagcagaagg tatgcttcct ggtaccagca gaagccaggc    120
caggcccctg tgctgctcat ctacagggat accagtcggc cctcagggct ccctgaccgc    180
ttctctggct ccagctcagg gaacacggcc accctgacca tcagtggggc ccaggctggg    240
gacgaggctg actactattg tgctacaagc gatggcagtg cagcagcta tcagtttgtg    300 ttcggcggag ggacccagct gaccgtcaca                                    330
```

<210> SEQ ID NO 18
<211> LENGTH: 360
<212> TYPE: DNA
<213> ORGANISM: Artificial Sequence
<220> FEATURE:
<223> OTHER INFORMATION: heavy chain variable region of R-88 antibody

<400> SEQUENCE: 18

```
cagtcggtgg aggagtccgg gggtcgcctg gtcacgcctg gacacccct gacactcacc    60 tgcacagtct ctggattctc cctcagtagc tatgcaatga gttgggtccg ccaggctcca    120
gggaaggggc tggaatggat cggactcatt agtagtagtg gtagcgcata ctacgcgagc    180
tgggcgaaag gccgattcac catctccaac ccctcgtcga ccacggtgga tctcaaaatc    240
accagtccga caaccgagga cacggccacc tatttctgcg ccagatacct ttacgagagt    300
gatggttatg ttaatgccct tgacttgtgg ggcccaggca cctggtcac cgtctcctca    360
```

<210> SEQ ID NO 19
<211> LENGTH: 330
<212> TYPE: DNA
<213> ORGANISM: Artificial Sequence
<220> FEATURE:

<223> OTHER INFORMATION: light chain variable region of O-1 antibody

<400> SEQUENCE: 19

```
cagtctgtgc tgactcagcc accctcagcg tctgggaccc ccgggcagag ggtcaccatc      60
tcttgtactg gctcttcatc taatattggc agtaattctg tcacctggta ccagcagctc     120
ccaggaacgg cccccaaact cctcatctat gatgatagta agcggccaag cggggtccct     180
gaccgattct ctggctccaa gtctggcacc tcagcctccc tggccatcag tgggctccgg     240
tccgaggatg aggctgatta ttactgtggt gcttgggatg atagcctgag tggttatgtc     300
ttcggcggag gcaccaagct gacggtccta                                      330
```

<210> SEQ ID NO 20
<211> LENGTH: 363
<212> TYPE: DNA
<213> ORGANISM: Artificial Sequence
<220> FEATURE:
<223> OTHER INFORMATION: heavy chain variable region of O-1 antibody

<400> SEQUENCE: 20

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg gtctcagcg atctcttatg ataatggtaa tacatattac     180
gctgattctg taaaaggtcg gttcaccatc tccagagaca attccaagaa cacgctgtat     240
ctgcaaatga acagcctgag agccgaggac acggccgtgt attactgtgc gagagatggt     300
atgtggaatg aggttagtgc gttcgactac tggggccagg gtacactggt caccgtgagc     360
tca                                                                   363
```

<210> SEQ ID NO 21
<211> LENGTH: 330
<212> TYPE: DNA
<213> ORGANISM: Artificial Sequence
<220> FEATURE:
<223> OTHER INFORMATION: light chain variable region of O-13 antibody

<400> SEQUENCE: 21

```
cagtctgtgc tgactcagcc accctcagcg tctgggaccc ccgggcagag ggtcaccatc      60
tcttgtagtg gctcttcatc taatattggc agtaatgatg tcaactggta ccagcagctc     120
ccaggaacgg cccccaaact cctcatctat tatgatagta agcggccaag cggggtccct     180
gaccgattct ctggctccaa gtctggcacc tcagcctccc tggccatcag tgggctccgg     240
tccgaggatg aggctgatta ttactgtct acttgggatg atagcctgag tgcttatgtc     300
ttcggcggag gcaccaagct gacggtccta                                      330
```

<210> SEQ ID NO 22
<211> LENGTH: 363
<212> TYPE: DNA
<213> ORGANISM: Artificial Sequence
<220> FEATURE:
<223> OTHER INFORMATION: heavy chain variable region of O-13 antibody

<400> SEQUENCE: 22

```
gaggtgcagc tgttggagtc tgggggaggc ttggtacagc ctggggggtc cctgagactc      60
tcctgtgcag cctctggatt cacctttagc agttatgata tgagctgggt ccgccaggct     120
ccagggaagg ggctggagtg gtctcagcg atctcttatg ataatggtaa tacatattac     180
gctgattctg taaaaggtcg gttcaccatc tccagagaca attccaagaa cacgctgtat     240
```

```
ctgcaaatga acagcctgag agccgaggac acggccgtgt attactgtgc gaaagatggt    300
tatcataatg agattgctcc gttcgactac tggggccagg gtacactggt caccgtgagc    360
tca                                                                   363
```

```
<210> SEQ ID NO 23
<211> LENGTH: 330
<212> TYPE: DNA
<213> ORGANISM: Artificial Sequence
<220> FEATURE:
<223> OTHER INFORMATION: light chain variable region of O-26 antibody

<400> SEQUENCE: 23
cagtctgtgc tgactcagcc accctcagcg tctgggaccc ccgggcagag ggtcaccatc     60
tcttgtactg gctcttcatc taatattggc agtaatgatg tcacctggta ccagcagctc    120
ccaggaacgg cccccaaact cctcatctat tctgatagtc atcggccaag cggggtccct    180
gaccgattct ctggctccaa gtctggcacc tcagcctccc tggccatcag tgggctccgg    240
tccgaggatg aggctgatta ttactgtgct gcttgggatg atagcctgag tggttatgtc    300
ttcggcggag gcaccaagct gacggtccta                                     330
```

```
<210> SEQ ID NO 24
<211> LENGTH: 363
<212> TYPE: DNA
<213> ORGANISM: Artificial Sequence
<220> FEATURE:
<223> OTHER INFORMATION: heavy chain variable region of O-26 antibody

<400> SEQUENCE: 24
gaggtgcagc tgttggagtc tgggggaggc ttggtacagc ctggggggtc cctgagactc     60
tcctgtgcag cctctggatt cacctttagc agttatgata tgagctgggt ccgccaggct    120
ccagggaagg ggctggagtg ggtctcagcg atctcttatg ataatggtaa tacatattac    180
gctgattctg taaaaggtcg gttcaccatc tccagagaca attccaagaa cacgctgtat    240
ctgcaaatga acagcctgag agccgaggac acggccgtgt attactgtgc gaaagatggt    300
cttgagaatg agacggctgg gttcgactac tggggccagg gtacactggt caccgtgagc    360
tca                                                                   363
```

```
<210> SEQ ID NO 25
<211> LENGTH: 321
<212> TYPE: DNA
<213> ORGANISM: Artificial Sequence
<220> FEATURE:
<223> OTHER INFORMATION: light chain variable region of J-1 antibody

<400> SEQUENCE: 25
gacatccaga tgacccagtc cccctcctcc ctgtccgcct ccgtgggcga ccgcgtgacc     60
atcacctgca gagcatcaca agatgtaaat acagcagtag catggtacca gcagaagccc    120
ggcaaggccc ccaagctgct gatctactca gcatcatttt tatattcagg cgtgccctcc    180
cgcttctccg gctcccgctc cggcaccgac ttcaccctga ccatctcctc cctgcagccc    240
gaggacttcg ccacctacta ctgccaacaa cattatacaa caccaccaac cttcggccag    300
ggcaccaagg tggagatcaa g                                              321
```

```
<210> SEQ ID NO 26
<211> LENGTH: 363
<212> TYPE: DNA
```

```
<213> ORGANISM: Artificial Sequence
<220> FEATURE:
<223> OTHER INFORMATION: heavy chain variable region of J-1 antibody

<400> SEQUENCE: 26
gaggtgcagc tggtggagtc cggcggcggc ctggtgcagc ccggcggctc cctgcgcctg      60
tcctgcgccg cctccggttt taatattaaa gatacatata ttcattgggt gcgccaggcc     120
cccggcaagg gcctggagtg ggtggccaga atttatccaa caaatggtta tacaagatat     180
gcagattcag taaaaggtcg cttcaccatc tccgccgaca cctccaagaa caccgcctac     240
ctgcagatga actccctgcg cgccgaggac accgccgtgt actactgctc ccgcggtgtt     300
ggtaaatctc gtcatcagcg tttcgactac tggggccagg gcaccctggt gaccgtgtcc     360
tcc                                                                   363

<210> SEQ ID NO 27
<211> LENGTH: 333
<212> TYPE: DNA
<213> ORGANISM: Artificial Sequence
<220> FEATURE:
<223> OTHER INFORMATION: light chain variable region of O-13(humanized)
      antibody

<400> SEQUENCE: 27
gacatccaga tgacccagtc ccctcctcg ctgagcgcct ccgtgggcga ccgggtgacc       60
atcacctgca gtggctcttc atctaatatt ggcagtaatg atgtcaactg gtatcagcag     120
aagcctggca aggcgcctaa gctgctgatc tactatgata gtaagcggcc aagcggcgtg     180
ccttcccggt tctccggatc ccggtccggc accgacttca ccctgaccat ctcctccctg     240
caacctgagg acttcgccac ctactactgc gctacttggg atgatagcct gagtgcttat     300
gtcttcggcc agggtaccaa ggtggagatc aag                                  333

<210> SEQ ID NO 28
<211> LENGTH: 363
<212> TYPE: DNA
<213> ORGANISM: Artificial Sequence
<220> FEATURE:
<223> OTHER INFORMATION: heavy chain variable region of O-13(humanized)
      antibody

<400> SEQUENCE: 28
gaggtgcagc tggtggagtc tggcggcgga ctggtgcagc ctggcggaag cttgcggctg      60
tcctgcgccg cctccggatt cacctttagc agttatgata tgagctgggt gcggcaggcc     120
cctggcaagg gcctcgagtg ggtggccgcg atctcttatg ataatggtaa tacatattac     180
gctgattctg taaaaggtcg gttcaccatc tccgccgaca cctccaagaa caccgcctac     240
ctgcagatga actccctgcg ggccgaggac accgccgtgt actactgctc cagagatggt     300
tatcataatg agattgctcc gttcgactac tggggccagg gcacactagt gaccgtgtcc     360
tcc                                                                   363

<210> SEQ ID NO 29
<211> LENGTH: 29
<212> TYPE: DNA
<213> ORGANISM: Artificial Sequence
<220> FEATURE:
<223> OTHER INFORMATION: Forward primer for PCR

<400> SEQUENCE: 29
cccaagctta tgagccgcac agcctacac                                        29
```

<210> SEQ ID NO 30
<211> LENGTH: 29
<212> TYPE: DNA
<213> ORGANISM: Artificial Sequence
<220> FEATURE:
<223> OTHER INFORMATION: Reverse primer for PCR

<400> SEQUENCE: 30
ccgctcgaga tccaaatcga tggatatgc                                29

<210> SEQ ID NO 31
<211> LENGTH: 27
<212> TYPE: DNA
<213> ORGANISM: Artificial Sequence
<220> FEATURE:
<223> OTHER INFORMATION: Forward primer for PCR (Gremlin-1)

<400> SEQUENCE: 31
ggccccaccg gccccatcca aatcgat                                  27

<210> SEQ ID NO 32
<211> LENGTH: 30
<212> TYPE: DNA
<213> ORGANISM: Artificial Sequence
<220> FEATURE:
<223> OTHER INFORMATION: Reverse primer for PCR (Gremlin-1)

<400> SEQUENCE: 32
ggggccggtg gggcctcggg tggcggtggc                               30

<210> SEQ ID NO 33
<211> LENGTH: 39
<212> TYPE: DNA
<213> ORGANISM: Artificial Sequence
<220> FEATURE:
<223> OTHER INFORMATION: Forward primer for PCR (IgG-Fc)

<400> SEQUENCE: 33
aagcttgtgg cccaggcggc catgagccgc acagcctac                     39

<210> SEQ ID NO 34
<211> LENGTH: 30
<212> TYPE: DNA
<213> ORGANISM: Artificial Sequence
<220> FEATURE:
<223> OTHER INFORMATION: Reverse primer for PCR (IgG-Fc)

<400> SEQUENCE: 34
ggatcctcat tttggcgggg acagggagag                               30

<210> SEQ ID NO 35
<211> LENGTH: 20
<212> TYPE: DNA
<213> ORGANISM: Artificial Sequence
<220> FEATURE:
<223> OTHER INFORMATION: Forward primer for PCR (VEGFR-2)

<400> SEQUENCE: 35
tgatcggaaa tgacactgga                                          20

<210> SEQ ID NO 36
<211> LENGTH: 20
<212> TYPE: DNA
<213> ORGANISM: Artificial Sequence
<220> FEATURE:

```
<223> OTHER INFORMATION: Reverse primer for PCR (VEGFR-2)

<400> SEQUENCE: 36
tgcttcacag aagaccatgc                                              20

<210> SEQ ID NO 37
<211> LENGTH: 20
<212> TYPE: DNA
<213> ORGANISM: Artificial Sequence
<220> FEATURE:
<223> OTHER INFORMATION: Forward primer for PCR (Gremlin-1)

<400> SEQUENCE: 37
aacagtcgca ccatcatcaa                                              20

<210> SEQ ID NO 38
<211> LENGTH: 20
<212> TYPE: DNA
<213> ORGANISM: Artificial Sequence
<220> FEATURE:
<223> OTHER INFORMATION: Reverse primer for PCR (Gremlin-1)

<400> SEQUENCE: 38
aatttcttgg gcttgcagaa                                              20

<210> SEQ ID NO 39
<211> LENGTH: 21
<212> TYPE: DNA
<213> ORGANISM: Artificial Sequence
<220> FEATURE:
<223> OTHER INFORMATION: Forward primer for PCR (GAPDH)

<400> SEQUENCE: 39
aggtgaaggt cggagtcaac g                                            21

<210> SEQ ID NO 40
<211> LENGTH: 20
<212> TYPE: DNA
<213> ORGANISM: Artificial Sequence
<220> FEATURE:
<223> OTHER INFORMATION: Reverse primer for PCR (GAPDH)

<400> SEQUENCE: 40
aggggtcatt gatggcaaca                                              20
```

GREMLIN-1 ANTIBODY

RELATED APPLICATIONS

This application is the National Stage of International Application. No. PCT/KR2013/002119, filed 15 Mar. 2013, which claims benefit of priority to U.S. Provisional Patent Application No. 61/611,285, filed 15 Mar. 2012, the specification of which is incorporated by reference herein.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file was created on Sep. 15, 2014, is 27 kilobytes in size, and titled 426SEQUS1.txt. A substitute Sequence Listing is filed electronically herewith, the contents of which are incorporated by reference in their entirety. The electronic file was created on Jan. 30, 2015, is 27 kilobytes in size, and titled 426SEQUS2.txt.

TECHNICAL FIELD

The present invention relates to a gremlin-1 antibody, and more particularly, to a gremlin-1 antibody that has the effect of treating cancer by inhibiting gremlin-1 in a manner independent of bone morphogenetic protein (BMP) or vascular endothelial growth factor receptor-2 (VEGFR2).

BACKGROUND ART

Gremlin-1 (20.7 kDa), an antagonist of bone morphogenetic protein (BMP), is a protein consisting of 184 amino acids having a common structure with a cysteine rich region, a cysteine knot motif and members of the TGF-β superfamily. This protein is evolutionarily conserved and the human gremlin gene (GREM1) has been mapped to chromosome 15q13-q15 (Topol L Z et al., (1997) *Mol. Cell Biol.*, 17: 4801-4810; Topol L Z et al., *Cytogenet Cell Genet.*, 89: 79-84). Gremlin-1 is a secreted protein, and three isoforms have been reported (Topol L Z et al., *J. Biol. Chem.*, 275: 8785-8793). Isoform 1 is the most common isoform, and isoforms 2 and 3 have deletions of amino acids 39-79 and 10-79, respectively.

Gremlin-1 forms heterodimers with BMP-2, BMP-4 and BMP-7, and thus it inhibits that bone morphogenetic protein (BMP) binds to receptors on the cell surface (Stanley E et al., (1998) *Mech. Dev.*, 77: 173-184; Merino R et al., (1999) *Development*, 126: 5515-5522; Lappin D W et al., (2000) *Curr. Opin. Nephrol. Hypertens.*, 9: 469-472). In addition, gremlin-1 plays an important role in regulating BMPs during lung, limb and kidney development as well as during neural crest cell differentiation (Lu M M et al., (2001) *Dev. Dyn.*, 222: 667-680; Shi W et al., (2001) *Am. J. Physiol. Lung Cell Mol. Physiol.*, 280: L1030-1039). In addition to its antagonistic effect on soluble ligands, gremlin-1 interacts intracellularly with the BMP-4 precursor protein and downregulates BMP-4-mediated signaling activity in embryonic lungs (Sun J et al., (2006) *J. Biol. Chem.*, 281: 29349-29356). Gremlin-1 also interacts with Slit proteins, a family of secreted axonal guidance proteins, and acts as an inhibitor of monocyte chemotaxis (Chen B et al., (2004) *J. Immunol.*, 173: 5914-5917). Recently, it was reported that gremlin-1 binds vascular endothelial growth factor receptor-2 (VEGFR2) in a BMP-independent manner and modulates angiogenesis (Mitola S et al., (2010) *Blood*, 116: 3677-3680). Gremlin-1 is overexpressed in various human tumors including carcinomas of the cervix, endometrium, lung, ovary, kidney, breast, colon and pancreas (Namkoong H et al., (2006) *BMC Cancer*, 6: 74; Sha G et al., (2009) *Fertil Steril.*, 91: 350-358), but its role in carcinogenesis has not been studied in detail.

The present inventors have studied the tumor-related characteristics of gremlin-1, and as a result, have found that gremlin-1 interacts directly with cancer cells in a BMP- or VEGFR2-independent manner, and based on this finding, have a neutralizing antibody capable of inhibiting gremlin-1.

SUMMARY OF INVENTION

The present invention provides a gremlin-1 antibody that has the effect of treating cancer or immune disease by inhibiting gremlin-1 in a manner independent of bone morphogenetic protein (BMP) or vascular endothelial growth factor receptor-2 (VEGFR2).

The present invention also provides a pharmaceutical composition for preventing or treating cancer or immune disease, comprising the gremlin-1 antibody and a pharmaceutically acceptable additive.

The present invention also provides a method for preventing or treating cancer or immune disease, comprising administration to a subject in need thereof the gremlin-1 antibody or a pharmaceutical composition comprising the gremlin-1 antibody.

The present invention also provides a kit for diagnosing cancer or immune disease, comprising the gremlin-1 antibody.

The gremlin-1 antibody according to the present invention can inhibit the binding of gremlin-1 to cancer cells in a manner independent of bone morphogenetic protein (BMP) or vascular endothelial growth factor receptor-2 (VEGFR2), and thus can be effectively used for the prevention or treatment of various cancers or immune diseases, which are mediated by gremlin-1.

DETAILED DESCRIPTION OF INVENTION

Figure 1:
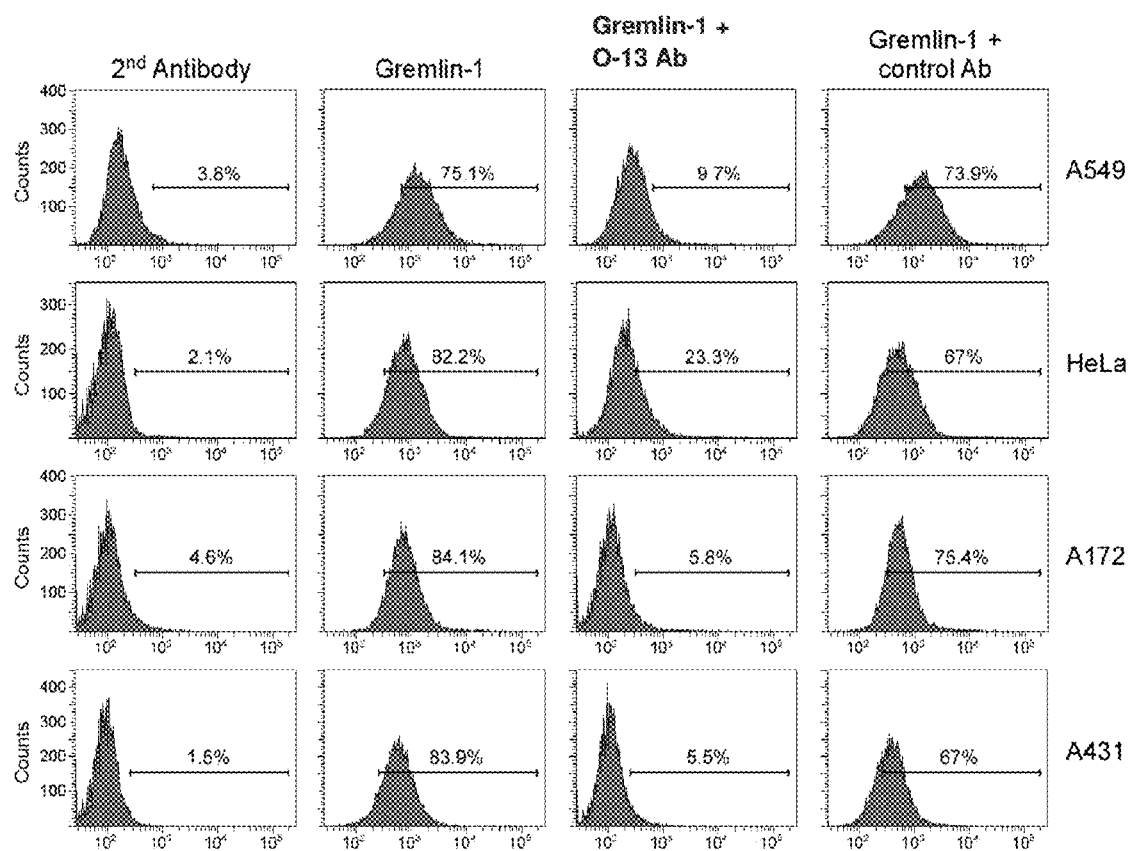
FIG. 1 is a graph showing the results obtained by treating four kinds of cancer cells (A549, HeLa, A172 and A431) with each of secondary antibody, gremlin-1 alone, and a combination of gremlin-1 with an antibody according to the present invention or a control antibody, and then analyzing the cells by flow cytometry.

Hereinafter, the present invention will be described in detail.

The present invention provides a gremlin-1 antibody. This antibody is characterized by having the effect of treating cancer by inhibiting gremlin-1 in a manner independent of bone morphogenetic protein (BMP) or vascular endothelial growth factor receptor-2 (VEGFR2). The antibody may be an immune antibody, a chimera antibody, a human antibody or a humanized antibody, but is not limited thereto.

The gremlin-1 antibody can be selected using, for example, phage-display technology. Namely, it can be selected by fusing a gene expressing the desired antibody to a gene expressing a filamentous phage coat protein, producing antibody-phage-type virus particles having the fused antibody exposed to the surface of bacteriophage particles, and then selecting the desired antibody from the phage library using a biopanning technique. Using the phage-display technology as described above, a large number of antibodies having excellent effects can be obtained, and among them, 7 kinds of antibodies having significantly excellent effects were selected.

The antibody may be an antibody comprising a light-chain constant region, a heavy-chain constant region, a light-chain variable region and a heavy-chain variable region, in which the light-chain variable region and the heavy-chain variable region are selected from among those having the following amino acid sequences, respectively:

(1) an antibody comprising a light-chain variable region having an amino acid sequence of SEQ ID NO: 1 and a heavy-chain variable region having an amino acid sequence of SEQ ID NO: 2;

(2) an antibody comprising a light-chain variable region having an amino acid sequence of SEQ ID NO: 3 and a heavy-chain variable region having an amino acid sequence of SEQ ID NO: 4;

(3) an antibody comprising a light-chain variable region having an amino acid sequence of SEQ ID NO: 5 and a heavy-chain variable region having an amino acid sequence of SEQ ID NO: 6;

(4) an antibody comprising a light-chain variable region having an amino acid sequence of SEQ ID NO: 7 and a heavy-chain variable region having an amino acid sequence of SEQ ID NO: 8;

(5) an antibody comprising a light-chain variable region having an amino acid sequence of SEQ ID NO: 9 and a heavy-chain variable region having an amino acid sequence of SEQ ID NO: 10;

(6) an antibody comprising a light-chain variable region having an amino acid sequence of SEQ ID NO: 11 and a heavy-chain variable region having an amino acid sequence of SEQ ID NO: 12; and (7) an antibody comprising a light-chain variable region having an amino acid sequence of SEQ ID NO: 13 and a heavy-chain variable region having an amino acid sequence of SEQ ID NO: 14.

In the present invention, antibodies (1) to (7) as described above were termed R-80, R-88, O-1, O-13, O-26, J-1, and O-13 (humanized), respectively.

The light-chain variable region and heavy-chain variable region of the antibody may be of human or rabbit origin. The light-chain variable region and heavy-chain variable region of the antibody may be used alone or in combination thereof, may be used in combination with the light-chain constant region and heavy-chain constant region known in the art, or fragments thereof may also be used. The light-chain variable region and the heavy-chain variable region may be produced in the form of single-chain variable fragment (scFv) according to a known method.

In the light-chain variable region having the amino acid sequence of SEQ ID NO: 1, amino acids 1-22 correspond to framework region 1 (FR1), amino acids 23-33 correspond to complementarity-determining region 1 (CDR1), amino acids 34-48 correspond to framework region 2 (FR2), amino acids 49-55 correspond to complementarity-determining region 2 (CDR2), amino acids 56-87 correspond to framework region 3 (FR3), amino acids 88-100 correspond to complementarity-determining region 3 (CDR3), and amino acids 101-110 correspond to framework region 4 (FR4).

In the heavy-chain variable region having the amino acid sequence of SEQ ID NO: 2, amino acids 1-24 correspond to FR1, amino acids 25-34 correspond to CDR1, amino acids 35-48 correspond to FR2, amino acids 49-64 correspond to CDR2, amino acids 65-95 correspond to FR3, amino acids 96-105 correspond to CDR3, and amino acids 106-116 correspond to FR4.

In the light-chain variable region having the amino acid sequence of SEQ ID NO: 3, amino acids 1-22 correspond to FR1, amino acids 23-33 correspond to CDR1, amino acids 34-48 correspond to FR2, amino acids 49-55 correspond to CDR2, amino acids 56-87 correspond to FR3, amino acids 88-100 correspond to CDR3, and amino acids 101-110 correspond to FR4.

In the heavy-chain variable region having the amino acid sequence of SEQ ID NO: 4, amino acids 1-24 correspond to FR1, amino acids 25-34 correspond to CDR1, amino acids 35-48 correspond to FR2, amino acids 49-64 correspond to CDR2, amino acids 65-95 correspond to FR3, amino acids 96-109 correspond to CDR3, and amino acids 110-120 correspond to FR4.

In the light-chain variable region having the amino acid sequence of SEQ ID NO: 5, amino acids 1-22 correspond to FR1, amino acids 23-35 correspond to CDR1, amino acids 36-50 correspond to FR2, amino acids 51-57 correspond to CDR2, amino acids 58-89 correspond to FR3, amino acids 90-100 correspond to CDR3, and amino acids 101-110 correspond to FR4.

In the heavy-chain variable region having the amino acid sequence of SEQ ID NO: 6, amino acids 1-25 correspond to FR1, amino acids 26-35 correspond to CDR1, amino acids 36-49 correspond to FR2, amino acids 50-66 correspond to CDR2, amino acids 67-98 correspond to FR3, amino acids 99-110 correspond to CDR3, and amino acids 111-122 correspond to FR4.

In the light-chain variable region having the amino acid sequence of SEQ ID NO: 7, amino acids 1-22 correspond to FR1, amino acids 23-35 correspond to CDR1, amino acids 36-50 correspond to FR2, amino acids 51-57 correspond to CDR2, amino acids 58-89 correspond to FR3, amino acids 90-100 correspond to CDR3, and amino acids 101-110 correspond to FR4.

In the heavy-chain variable region having the amino acid sequence of SEQ ID NO: 8, amino acids 1 to 25 correspond to FR1, amino acids 26-35 correspond to CDR1, amino acids 36-49 correspond to FR2, amino acids 50-66 correspond to CDR2, amino acids 67-98 correspond to FR3, amino acids 99-110 correspond to CDR3, and amino acids 111-121 correspond to FR4.

In the light-chain variable region having the amino acid sequence of SEQ ID NO: 9, amino acids 1-22 correspond to FR1, amino acids 23-35 correspond to CDR1, amino acids 36-50 correspond to FR2, amino acids 51-57 correspond to CDR2, amino acids 58-89 correspond to FR3, amino acids 90-100 correspond to CDR3, and amino acids 101-110 correspond to FR4.

In the heavy-chain variable region having the amino acid sequence of SEQ ID NO: 10, amino acids 1-25 correspond to FR1, amino acids 26-35 correspond to CDR1, amino acids 36-49 correspond to FR2, amino acids 50-66 correspond to CDR2, amino acids 67-98 correspond to FR3, amino acids 99-110 correspond to CDR3, and amino acids 111-121 correspond to FR4.

In the light-chain variable region having the amino acid sequence of SEQ ID NO: 11, amino acids 1-23 correspond to FR1, amino acids 24-34 correspond to CDR1, amino acids 35-49 correspond to FR2, amino acids 50-56 correspond to CDR2, amino acids 57-88 correspond to FR3, amino acids 89-97 correspond to CDR3, and amino acids 98-107 correspond to FR4.

In the heavy-chain variable region having the amino acid sequence of SEQ ID NO: 12, amino acids 1-30 correspond to FR1, amino acids 31-35 correspond to CDR1, amino acids 36-49 correspond to FR2, amino acids 50-66 correspond to CDR2, amino acids 67-98 correspond to FR3, amino acids 99-110 correspond to CDR3, and amino acids 111-121 correspond to FR4.

In the light-chain variable region having the amino acid sequence of SEQ ID NO: 13, amino acids 1-23 correspond to FR1, amino acids 24-36 correspond to CDR1, amino acids 37-51 correspond to FR2, amino acids 52-58 correspond to CDR2, amino acids 59-90 correspond to FR3, amino acids 91-101 correspond to CDR3, and amino acids 102-111 correspond to FR4.

In the heavy-chain variable region having the amino acid sequence of SEQ ID NO: 14, amino acids 1-25 correspond to FR1, amino acids 26-35 correspond to CDR1, amino acids 36-49 correspond to FR2, amino acids 50-66 correspond to CDR2, amino acids 67-98 correspond to FR3, amino acids 99-110 correspond to CDR3, and amino acids 111-121 correspond to FR4.

The amino acid sequence of SEQ ID NO: 1 may be encoded by a nucleotide sequence of SEQ ID NO: 15; the amino acid sequence of SEQ ID NO: 2 may be encoded by a nucleotide sequence of SEQ ID NO: 16; the amino acid sequence of SEQ ID NO: 3 may be encoded by a nucleotide sequence of SEQ ID NO: 17; the amino acid sequence of SEQ ID NO: 4 may be encoded by a nucleotide sequence of SEQ ID NO: 18; the amino acid sequence of SEQ ID NO: 5 may be encoded by a nucleotide sequence of SEQ ID NO: 19; the amino acid sequence of SEQ ID NO: 6 may be encoded by a nucleotide sequence of SEQ ID NO: 20; the amino acid sequence of SEQ ID NO: 7 may be encoded by a nucleotide sequence of SEQ ID NO: 21; the amino acid sequence of SEQ ID NO: 8 may be encoded by a nucleotide sequence of SEQ ID NO: 22; the amino acid sequence of SEQ ID NO: 9 may be encoded by a nucleotide sequence of SEQ ID NO: 23; the amino acid sequence of SEQ ID NO: 10 may be encoded by a nucleotide sequence of SEQ ID NO: 24; the amino acid sequence of SEQ ID NO: 11 may be encoded by a nucleotide sequence of SEQ ID NO: 25; the amino acid sequence of SEQ ID NO: 12 may be encoded by a nucleotide sequence of SEQ ID NO: 26; the amino acid sequence of SEQ ID NO: 13 may be encoded by a nucleotide sequence of SEQ ID NO: 27; and the amino acid sequence of SEQ ID NO: 14 may be encoded by a nucleotide sequence of SEQ ID NO: 28.

Gremlin-1 is known to be expressed in cancer tissue, but the specific role thereof has not yet been identified. Gremlin-1 is known as an antagonist of bone morphogenetic protein (BMP), and it was reported that gremlin-1 binds to vascular endothelial growth factor receptor-2 (VEGFR2) to regulate vascular formation. Thus, it was expected that gremlin-1 interact with cancer cells in a BMP- or VEGFR2-dependent manner. However, surprisingly, the present inventors have found that gremlin-1 binds directly to cancer cells in a BMP- or VEGFR2-independent manner to induce cell migration, invasion and proliferation. In addition, gremlin-1 induces the growth of cancer cells by inhibiting the expression of E-cadherin.

The cell migration, invasion and proliferation are inhibited by the gremlin-1 antibody as described above. Thus, the gremlin antibody can exhibit the effect of treating cancer by inhibiting gremlin-1 in a BMP- or VEGFR2-independent manner, that is, inhibiting the direct binding of gremlin-1 to cancer cells.

The present invention provides a pharmaceutical composition for preventing or treating cancer, which comprises gremlin-1 antibody and a pharmaceutically acceptable additive. The additive may include a carrier, an excipient or other additives. The composition of the present invention can be prepared as a pharmaceutical formulation according to a conventional method. In the preparation of the formulation, the antibody is preferably mixed or diluted with a carrier or enclosed in a container-type carrier. If a carrier is used as a diluent, it may be a solid, semi-solid or liquid material acting as a carrier, excipient or medium for the antibody. Thus, the formulation may be in the form of tablet, pill, powder, sachet, elixir, suspension, emulsion, solution, syrup, aerosol, soft or hard gelatin capsule, sterile injectable solution, sterile powder or the like. Examples of suitable carriers, excipients and diluents include lactose, dextrose, sucrose, sorbitol, mannitol, calcium silicate, cellulose, methylcellulose, microcrystalline cellulose, polyvinyl-pyrrolidone, water, methylhydroxybenzoate, propylhydroxy-benzoate, talc, magnesium stearate and mineral oil. The pharmaceutical composition of the present invention may additionally include fillers, anti-agglutinating agents, lubricants, wetting agents, flavoring agents, emulsifiers, preservatives and the like. The composition of the present invention may be formulated using a method well-known in the art such that it provides quick, sustained or delayed release of the antibody after its administration to a mammal. The antibody composition of the present invention may comprise, in addition to the above-described antibody, an antiviral agent such as interferon, an HBV monoclonal antibody, an HBV polyclonal antibody, a nucleoside analogue, a DNA polymerase inhibitor, an siRNA drug, or a therapeutic vaccine.

An antibody according to the present invention or a pharmaceutical composition comprising the same may be administered to subjects in need thereof, for example, mammals including humans, in order to treat cancer. The dose of the antibody is determined according to the subject to be treated, the severity of the disease or condition, the rate of administration, and the judgment of the physician. The antibody as an active ingredient can be administered parenterally in an amount of about 0.001 to 10 mg/kg (body weight), preferably 0.005 to 1 mg/kg, in a single dose or in divided doses per day. In some cases, the antibody may be administered in an amount smaller than the lower limit of the above-mentioned range and may be administered in an amount larger than the upper limit, as long as it does not cause serious side effects. If the antibody is administered in an amount larger than the upper limit, it may be administered several times a day.

Therefore, the present invention provides a method for treating cancer, which comprises administering to a subject in need thereof the antibody according to the present invention or the above-described pharmaceutical composition. Herein, the antibody according to the present invention is characterized by having the effect of treating cancer by inhibiting gremlin-1 in a manner independent of bone morphogenetic protein (BMP) or vascular endothelial growth factor receptor-2 (VEGFR2).

Examples of the above-described cancer include, but are not limited to, prostate cancer, pancreatic cancer, lung cancer, non-small-cell lung cancer, stomach cancer, liver cancer, kidney cancer, ovarian cancer, colorectal cancer, rectal cancer, breast cancer, thyroid cancer, skin cancer, bone cancer, basal cell carcinoma, squamous cell carcinoma, nasopharyngeal carcinoma, bladder cancer, uterine cancer, esophagus cancer, and head and neck cancer.

Meanwhile, the antibody of the present invention may be used for the prevention or treatment of immune diseases. A number of literatures demonstrated that gremlin-1 is closely associated with immune diseases (Mezzano S, et al. (2007) Expression of gremlin, a bone morphogenetic protein antagonist, in glomerular crescents of pauci-immune glomerulonephritis. Nephrology, dialysis, transplantation: official publication of the European Dialysis and Transplant Association-European Renal Association 22(7):1882-1890).

Thus, the gremlin-1 antibody according to the present invention may be used for the prevention or treatment of immune disease.

Examples of the immune disease include, but not limited to, rheumatoid arthritis, progressive systemic sclerosis (scleroderma), systemic lupus erythematosus, atopic dermatitis, alopecia areata, psoriasis, pemphigus, asthma, aphthous stomatitis, chronic thyroiditis, acquired aplastic anemia, primary cirrhosis, ulcerative colitis, Behcet's disease, Crohn's disease, silicosis, asbestosis, IgA nephropathy, post-streptococcal glomerulonephritis (PSGN), Sjogren's syndrome, Guillian-Barre syndrome, dermatomyositis, polymyositis, multiple sclerosis, autoimmune hemolytic anemia, autoimmune encephalomyelitis, myasthenia gravis, Grave's disease, polyarteritis nodosa, ankylosing spondylitis, fibromyalgia syndrome and temporal arteritis.

Meanwhile, the present invention provides a kit for diagnosing cancer or immune disease, which comprises the antibody of the present invention. The kit may comprise, in addition to the antibody of the present invention, conventional reagents for immunohistochemical staining. Components that may additionally included in the kit include, but are not limited to, FITC reagent, an antigen retrieval solution, a control antibody, a HRP-conjugated polymer, a DAB solution (3-3'-diaminobezidine tetrachloride), a Mayer's hematoxylin solution, etc. When the kit is used, a normal tissue and a tissue for diagnosis is treated with the labeled antibody according to the present invention, stained, and observed with a microscope, and the tissue that interacted with the antibody according to the present invention can be diagnosed as a tissue afflicted with cancer or immune disease.

Hereinafter, the present invention will be described in detail with reference to examples. It is to be understood, however, that these examples are for illustrative purposes and are not intended to limit the scope of the present invention.

Example 1: Expression and Purification of Gremlin-1

1-1: Cell Culture

A549, HeLa, A172 and A431 cells were obtained from the Korean Cell Line Bank (Seoul, Republic of Korea), and human umbilical vein endothelial cells (HUVECs) were obtained from Invitrogen (Carlsbad, Calif.). Meanwhile, A549, A172 and A431 cells were cultured in RPMI-1640 media (Welgene) supplemented with 10% FBS, and HeLa cells were cultured in MEM media (Welgene) supplemented with 10% FBS, and HUVECs were cultured in endothelial cell growth media-2 (EGM-2, Lonza, Walkersville, Md.).

1-2: Preparation of Gremlin-1 Expression Vector and Cell Transfection

The gremlin cDNA was amplified from a human cervical tissue cDNA library as described in Namkoong H et al., (2006) BMC Cancer 6: 74. Then, HindIII and XhoI restriction enzyme sites were introduced into the 5' and 3' ends of the gremlin cDNA by PCR using the following PCR primers:

(SEQ ID NO: 29)
5'-CCC AAG CTT ATG AGC CGC ACA GCC TAC AC-3';

(SEQ ID NO: 30)
5'-CCG CTC GAG ATC CAA ATC GAT GGA TAT GC-3'.

The PCR product was digested with HindIII and XhoI, and then ligated into the pcDNA3.1/myc-His vector (Invitrogen), thereby preparing a gremlin-1 expression vector.

1 day before transfection, A549 cells ($5.0\times10^5$ cells) were plated to achieve a confluency of 70%. Then, the prepared gremlin-1 expression vector was transfected into the A549 cells using the Lipofectamine 2000 reagent (Invitrogen) according to the manufacturer's instructions. The transfected cells were selected using 1.0 mg/ml of antibiotic G418 (Invitrogen). The selected cell line was termed "gremlin-1-A549 cell line".

Meanwhile, A549 cells were transfected with a pcDNA3.1/myc-His vector, which does not contain gremlin-1, in the same manner as described above, thereby obtaining a mock-A549 cell line.

1-3: Expression and Purification of Gremlin-1

A gene encoding human gremlin-1 and human IgG1-Fc fusion protein was constructed using overlapping PCR as described in Park S et al., (2010) Clin Chim Acta 411: 1238-1242. The linker primer sequences for gremlin-1 and IgG-Fc, used in the PCR, are as follows:

(1) Gremline-1
F:
(SEQ ID NO: 31)
5'-GGC CCC ACC GGC CCC ATC CAA ATC GAT-3';
R:
(SEQ ID NO: 32)
5'-GGG GCC GGT GGG GCC TCG GGT GGC GGT GGC-3';

(2) IgG-Fc
F:
(SEQ ID NO: 33)
5'-AAG CTT GTG GCC CAG GCG GCC ATG AGC CGC ACA GCC TAC-3';
R:
(SEQ ID NO: 34)
5'-GGA TCC TCA TTT TGG CGG GGA CAG GGA GAG-3'.

The PCR products were digested with HindIII and BamHI, and cloned into a pCEP4 expression vector (Invitrogen), thereby constructing a vector expressing the gremlin-1-Fc fusion protein.

Meanwhile, HEK293F cells (Invitrogen) were cultured in GIBCO FreeStyle™ 293 expression media (Invitrogen) at a cell density between $0.1\times10^6$ and $2.0\times10^6$ cells/ml, and then grown in disposable Erlenmeyer tissue culture flasks with vented caps (Corning Inc.) at 135 rpm on an orbital shaking incubator (37 37° C., 8% $CO_2$, Minitron, INFORSHT, Switzerland). One day prior to transfection, the cell cultures were diluted with fresh media to achieve a density of $1.0\times10^6$ cells/ml, which resulted in a density of $2.0\times10$ cells/ml on the day of transfection. Then, the HEK293F cells were transfected with the gremlin-1/human IgG-Fc fusion protein expression vector using Lipofectamine 2000 (Invitrogen). The transfected cells were cultured again in the orbital shaking incubator, and the culture supernatants were harvested at 3 days after transfection. Then, the gremlin-1-Fc fusion protein was purified using protein A affinity gel chromatography as described in Park S et al., (2010) Clin Chim Acta 411: 1238-1242.

Example 2: Generation of Gremlin-1 Antibody 2-1: Immunization

5 μg of gremlin-1-Fc was mixed with 2 mL of phosphate buffered saline (PBS) and incubated at 37° C. for 30 minutes, and the mixture was emulsified in an oil-in-water emulsion adjuvant (Sigma, St. Louis, Mo.) containing detoxified endotoxin MPL (monophosphorylate lipid A species) and mycobacterial cell wall components (TDW and CWS) in 2% squalene, and was then injected into New Zealand white rabbits. Immunization was performed three times at 3-week intervals. The antibody titer of the immunized rabbits was determined by an enzyme-linked immunosorbent assay (ELISA) using horseradish peroxidase (HRP)-conjugated mouse anti-rabbit IgG polyclonal antibody (Pierce Chemical Co., Rockford, Ill.) as secondary antibody.

Total RNA was obtained from the spleen and bone marrow of the immunized rabbits using TRI reagent (Invitrogen). The extracted spleen and bone marrow were homogenized in TRI reagent using a homogenizer at a 50% output for 1 minute and incubated at room temperature for 5 minutes. The homogenized samples were centrifuged at 2,500 g at 4° C. for 10 minutes. The supernatants were transferred into 50 mL centrifugation tubes, and 3 mL of 1-bromo-3-chloro-propane (BCP, Sigma) was added to each of the supernatants. Then, each of the mixtures was vortexed for 15 seconds and incubated at room temperature for 15 minutes. The mixture was centrifuged at 17,000 g at 4° C. for 15 minutes, and the colorless upper aqueous layer was transferred into a fresh 50 mL tube. Then, 15 mL of isopropanol was added to the aqueous layer and incubated at room temperature for 10 minutes. After centrifugation at 17,500 g at 4° C. for 15 minutes, the supernatant was carefully removed, and the pellet was washed with 30 mL of 75% ethanol without re-suspension. The pellet was centrifuged again for 10 minutes, and the supernatant was removed, after which the pellet was air-dried at room temperature. Next, the pellet was dissolved in RNase-free water and stored at −80° C. The optical density (OD) at 260 nm was measured to determine the RNA concentration (40 ng/μL RNA produces $OD_{260}=1$), and the purity was calculated by the $OD_{260}/OD_{280}$ ratio (generally ranging from 1.6 to 1.9).

2-2: Synthesis of First-Strand cDNA from Total RNA

First-strand cDNA was synthesized using the Superscript™ III system (Invitrogen) for the first-strand cDNA synthesis kit with oligo (dT) priming. 5 μg of the isolated total RNA was mixed with 1 μL of 0.5 μg/μL oligo (dT), 1 μL of 10 mM dNTP, and diethyl pyrocarbonate (DEPC)-treated water to make a final volume of 10 μL. The mixture was incubated at 65° C. for 5 minutes and cooled on ice. To the RNA sample, 2 μL of 10× reaction buffer, 4 μL of 25 mM $MgCl_2$, 2 μL of 100 mM dithiothreitol (DTT), 1 μL of RNase OUT (Ribonuclease Inhibitor) and 1 μL of Superscript III reverse transcriptase were added, and the mixture was incubated at 50° C. for 50 minutes. After incubation at 85° C. for 5 minutes, the reaction mixture was cooed on ice to stop the reaction. Then, 1 μL of RNase H was added thereto, followed by incubation at 37° C. for 20 minutes. The first-strand cDNA was stored at −20° C.

2-3: Primary PCR

The first-strand cDNA obtained from the spleen and bone marrow of the rabbits was subjected to PCR for 30 cycles using the Expand High Fidelity PCR system (Roche Molecular Systems, IN, USA). In the PCR, a combination of 10 primers for amplification of a rabbit $V_L$ ($9\times V_k$ and $1\times V_\lambda$) encoding sequence and a combination of 4 primers for amplification of a rabbit $V_H$ encoding sequence (Table 1) were also used. In each reaction, 1 μL of cDNA was mixed with 60 pmol of each primer, 10 μL of 10× reaction buffer, 8 μL of 2.5 mm dNTP (Promega, Madison, Wis.), 0.5 μL of Taq DNA polymerase, and water to make a final volume of 100 μL. The PCR was performed under the following conditions: 30 cycles, each consisting of 94° C. for 15 sec, 56° C. for 30 sec and 72° C. for 90 sec, and then final extension at 72° C. for 10 minutes. The fragments having a length of about 350 bp were loaded and electrophoresed on 1.5% agarose gel, and then purified using the QIAEX II gel extraction kit (QIAGEN, Valencia, Calif.). The purified PCR products were quantified at OD 260 nm (1 OD unit=50 μg/mL).

2-4: Secondary PCR

In secondary PCR, the primary $V_L$ products were randomly linked with the primary $V_H$ products by overlap extension PCR (Table 2). For a long linker single-chain fragment, at least 10 reactions were performed. In each reaction, 100 ng of the purified light-chain product or heavy-chain product was mixed with 60 pmol of each primer, 10 μL of 10× reaction buffer, 8 μL of 2.5 mM dNTP (Promega), 0.5 μL of Taq DNA polymerase, and water to make a final volume of 100 μL. PCR was performed under the following conditions: 20 cycles, each consisting of 94° C. for 15 sec, 56° C. for 30 sec and 72° C. for 2 min, followed by final extension at 72° C. for 10 min. About 700 bp fragments were loaded and electrophoresed on 1.5% agarose gel, and then purified using the QIAEX II gel extraction kit (QIAGEN, Valencia, Calif.). The purified PCR products were quantified at OD 260 nm (1 OD unit=50 μg/mL).

2-5: Treatment of Purified Overlap Extension Product and Vector DNA with Restriction Enzyme The PCR product and the pComb3x vector (The Scripps Research Institute) were treated with a SfiI restriction enzyme for cloning. 10 μg of the purified overlap PCR product was mixed with 360 units of SfiI (16 units per μg DNA, Roche Molecular Systems), 20 μL of 10× reaction buffer M, and water to make a final volume of 200 μL. 20 μg of the pComb3x vector was mixed with 120 units of SfiI (6 units per μg DNA, Roche Molecular Systems), 20 μL of 10× reaction buffer M, and water to make a final volume of 200 μL. The mixtures were incubated at 50° C. for 5 hours. The digested inserts having a length of about 700 bp were purified on 1% agarose gel, and about 3,400 bp vector DNA and about 1,600 bp fragment contained in the pComb3x vector were purified on 0.6% agarose gel.

2-6: Ligation of Treated Overlap PCR Product with Treated Vector DNA

In order to evaluate the suitability of the vector and the insert for high-efficiency ligation and transformation, small-scale ligation was performed. A ligation reaction containing the SfiI-treated vector DNA alone was evaluated for background ligation with a library size of less than 5%. For ligation, 140 ng of the SfiI-treated and purified vector DNA, 70 ng of the SfiI-treated and purified PCR product or stuffer DNA, 4 μL of 5× ligase buffer, 1 μL of T4 ligase (Invitrogen), and water were mixed to make a total volume of 20 μL. The mixture for ligation was incubated at room temperature for 4 hours. 1 μL of the ligated product was transformed into 50 μL of ER2738 electrocompetent cells (NEB) by electroporation 2.5 kV, 25 pF and 200Ω using a 0.2 cm cuvette and a gene pulser (Bio-Rad Laboratories, Hercules, Calif.). The cells were resuspended in 3 mL of SB medium and incubated at 37° C. for 1 hour with stirring at 225-250 rpm. 1 μL, 10 μL and 100 μL of the transformants were seeded in LB+carbenicillin plates to determine the total number of the transformants. Ideally, the size of the final library should be at least $10^8$ colony forming units (cfu) per μg of the vector DNA and should be less than 5% background ligation.

2-7: Construction of Electrocompetent E. coli

The E. coli ER2738 strain was cultured in a 50 mL polypropylene tube containing 15 mL of SB and was grown overnight at 37° C. with stirring at 250 rpm. On the next day, 2.5 mL of the culture was diluted into a 2 L flask containing 500 mL of SB, 10 mL of 20% (w/v) glucose and 5 mL of 1M $MgCl_2$, and was stirred at 250 rpm at 37° C. until the OD at 600 nm reached 0.8-0.9. Then, the culture was placed in a pre-cooled 500 mL centrifugation bottle and centrifuged at 3,000 g at 4 for 20 minutes. The supernatant was removed, and the pellet was re-suspended in 30 mL of pre-cooled 10% (v/v) glycerol. The re-suspended pellet was centrifuged, washed three times with glycerol, re-suspended in 5 mL of 10% glycerol, and stored at −80° C.

2-8: Preparation of Helper Phages

10 μL of the ER2738 suspension prepared in Example 2-7 was seeded into 10 mL of SB medium and stirred at 250 rpm at 37 for 1 hour. The single helper phage plaque obtained from the newly prepared plate was transferred into the culture using a pipette tip. 10 mL of the infected culture was transferred into a 2 L Erlenmeyer flask containing 500 mL of preheated (37° C.) SB medium containing kanamycin and was adjusted to a final concentration of 70 μg/mL, and then stirred at 250 rpm overnight at 37° C. On the next day, the culture was centrifuged at 2,500 g for 15 minutes, and the supernatant was incubated in a water bath at 70 for 20 minutes. After centrifugation at 2,500 g for 15 minutes, the supernatant was transferred into a fresh 50 mL polypropylene tube and stored at 4° C.

2-9: Library Ligation and Transformation

Library ligation was performed using 1.4 μg of SfiI-digested pComb3x, 700 ng of the SfiI-digested PCR product obtained in Example 2-5, 40 μL of 5× ligase buffer, 10 μL of T4 DNA ligase, and water (making a final volume of 200 μL). The mixture for ligation was incubated overnight at room temperature, and then allowed to precipitate with ethanol overnight at −80° C. After centrifugation in a microcentrifuge at the maximum speed for 15 minutes at 4 t, the supernatant was removed, and the pellet was washed with 1 mL of 70% (v/v) ethanol and dried. The pellet was dissolved in 15 μL of water. The ligated library sample was transformed into 300 μL of electrocompetent E. coli cells, which were then cultured in 5 mL of SB medium at 37° C. for 1 hour. 100 mL of preheated SB medium and 3 μL of 100 mg/mL carbenicillin were added to the culture. 0.1 μL, 1 μL and 10 μL of the culture were seeded on LB medium containing 50 μg/mL carbenicillin to determine the library size. The culture was stirred at 250 rpm for 1 hour. 4.5 μL of 100 mg/mL carbenicillin was added to the culture, which was then cultured for 1 hour. To the culture, 2 mL of VCSM13 helper phage, 183 mL of preheated SB and 92.5 μL of 100 mg/mL carbenicillin were added, and the mixture was stirred at 300 rpm and 37° C. for 2 hours. 280 μL of 50 mg/mL kanamycin was added to the culture, which was then stirred overnight at 300 rpm and 37° C. On the next day, the culture was centrifuged at 3,000 g at 4° C. for 15 minutes. The supernatant was transferred into a 500 mL centrifugation bottle, and then 8 g of polyethylene glycol (PEG)-8000 and 6 g of NaCl were added thereto. After storage on ice for 30 minutes, the supernatant was centrifuged at 15,000 g and 4 for 15 minutes. The supernatant was removed, and the phage pellet was re-suspended in Tris-buffer saline (TBS) containing 1% BSA.

2-10: Library Panning on Immobilized Antigen

Biopanning was performed using paramagnetic beads (Dynal Biotech, Lake Success, N.Y.). 3 µg of gremlin-1 was bound to 1×10$^7$ beads at room temperature for 20 hours. The beads were washed four times with PBS and incubated with blocking buffer at room temperature for 1 hour. The gremlin-1-bound beads were incubated with the scFv-displaying phages, obtained in Example 2-9, at room temperature for 2 hours. The washing steps were increased from three times in the first round to 10 times in the fourth round. The bound phages were eluted with 50 µL of 0.1 M glycine/HCl (pH 2.2) and neutralized with 3 µL of 2M Tris-HCl (pH 9.1). ER2738 was infected with this phage-containing supernatant, and the phagemids were rescued with helper phage VCSM13 for overnight amplification. On the next day, as described in Example 2-9, PEG-8000 and NaCl were added to prepare phages. In addition, the culture infected with the phages was seeded in an LB plate containing 50 µg/ml, carbenicillin to determine the input and output phage titers.

2-11: Selection of Clones by Phage ELISA

In order to confirm scFv binding from selected individual clones for additional analysis, ELISA was performed for the purified recombinant gremlin-1 using scFv-displaying phages. A microtiter plate coated with gremlin-1 was blocked with 3% BSA in PBS at 37° C. for 1 hour. Then, the phage supernatant was mixed with 6% BSA in PBS in the same manner, and incubated at 37° C. for 1 hour. After washing with 0.05% PBST, the plate was incubated with HRP-conjugated anti-M13 antibody (1:5000 dilution, Pierce Chemical Co.). For color reaction, 2,2'-azino-bis(3-ethyl-benzothiazoline-6-sulfonic acid, ABTS) substrate solution (Amresco, Solon, Ohio) was used.

The scFv fragments were converted to full-length IgG and overexpressed. The specificity of the antibody (O-13) of the present invention was determined using Western blot analysis. In order to determine the specificity of the antibody (O-13) of the present invention, the culture supernatant of the HEK293F cells transfected with pcDNA3.1/myc-His-gremlin-1 was isolated by SDS-PAGE. Blots were incubated with 100 ng/ml, of the antibody (O-13) according to the present invention overnight at 4° C., and then incubated with HRP-conjugated anti-human IgG (Fc specific, 1:1000 dilution; Pierce Chemical Co.) at room temperature for 1 hour. Blots were visualized using an enhanced chemiluminescence system (Pierce) according to the manufacturer's instructions. Gel was visualized using Coomassie brilliant blue G-250 (Sigma) according to according to the manufacturer's instructions.

The 7 antibodies obtained through the above-described procedures were termed R-80, R-88, O-1, O-13, O-26, J-1 and O-13 (humanized) antibodies, respectively, and the amino acid sequences and nucleotide sequences thereof were analyzed.

The results of the sequence analysis indicated that the R-80 antibody comprises a light-chain variable region having an amino acid sequence of SEQ ID NO: 1 and a heavy-chain variable region having an amino acid sequence of SEQ ID NO: 2; the R-88 antibody comprises a light-chain variable region having an amino acid sequence of SEQ ID NO: 3 and a heavy-chain variable region having an amino acid sequence of SEQ ID NO: 4; the O-1 antibody comprises a light-chain variable region having an amino acid sequence of SEQ ID NO: 5 and a heavy-chain variable region having an amino acid sequence of SEQ ID NO: 6; the O-13 antibody comprises a light-chain variable region having an amino acid sequence of SEQ ID NO: 7 and a heavy-chain variable region having an amino acid sequence of SEQ ID NO: 8; the O-26 antibody comprises a light-chain variable region having an amino acid sequence of SEQ ID NO: 9 and a heavy-chain variable region having an amino acid sequence of SEQ ID NO: 10; the J-1 antibody comprises a light-chain variable region having an amino acid sequence of SEQ ID NO: 11 and a heavy-chain variable region having an amino acid sequence of SEQ ID NO: 12; and the O-13 (humanized) antibody comprises a light-chain variable region having an amino acid sequence of SEQ ID NO: 13 and a heavy-chain variable region having an amino acid sequence of SEQ ID NO: 14.

The results of preliminary experiments indicated that the O-13 antibody had the best effect among the above antibodies. Thus, the O-13 antibody was used in subsequent experiments.

Example 3: Analysis of Interaction of Gremlin-1 with Cancer Cells

In order to examine whether gremlin-1 interacts directly with cancer cells, gremlin-1 was incubated with four kinds of cancer cells (A549, HeLa, A172 and A431), and then analyzed by flow cytometry.

Specifically, adherent cells were trypsinized and washed with 1% (w/v) BSA in phosphate buffered saline (PBS). Suspension cells were collected by centrifugation at 500×g for 2 min and washed with 1% (w/v) BSA in PBS. All cells were incubated with His-tagged gremlin-1 (R&D Systems, Minneapolis, Minn.) at a final concentration of 100 nM in 1% (w/v) BSA in PBS at 37° C. for 1 hour. The cells were then washed twice with 1% (w/v) BSA in PBS and incubated for 30 min at 37° C. in the dark with a FITC-conjugated His antibody (Abcam, Cambridge, UK) at a final concentration of 5 mg/ml. Then, the cells were washed twice with 1% (w/v) BSA in PBS and resuspended in 500 µL of PBS prior to analysis on a FACSCanto II flow cytometer (BD Biosciences, San Jose, Calif.).

Meanwhile, to determine the neutralizing efficacy of the gremlin-1 antibody (O-13), cells were incubated with 100 nM of His-tagged gremlin-1 and 10 pM of the antibody (O-13) according to the present invention in 1% (w/v) BSA in PBS for 1 hour at 37 r, and probed with a FITC-conjugated His antibody (Abcam).

A549 cells were treated with 1 pM of BMP-2, BMP-4, or BMP-7 (R&D Systems, Minneapolis, Minn.) and 100 nM of gremlin-1-Fc simultaneously and incubated for 1 hour at 37° C. The cells were probed with FITC-conjugated IgG-Fc specific antibody (5 µg/ml, Invitrogen). The cells were then analyzed on a FACSCanto II flow cytometer.

The results of the experiment are shown in FIG. 1. As can be seen in FIG. 1, gremlin-1 interacted directly with the cancer cells, and this interaction was inhibited by the gremlin-1 antibody.

Example 4: Effect of VEGFR2 on Interaction of Gremlin-1 with Cancer Cells

In order to examine whether the interaction of gremlin-1 with cell lines is mediated by VEGFR2 known as the sole cell surface receptor of gremlin-1, the following experiment was performed.

4-1: Flow Cytometry

Figure 2:
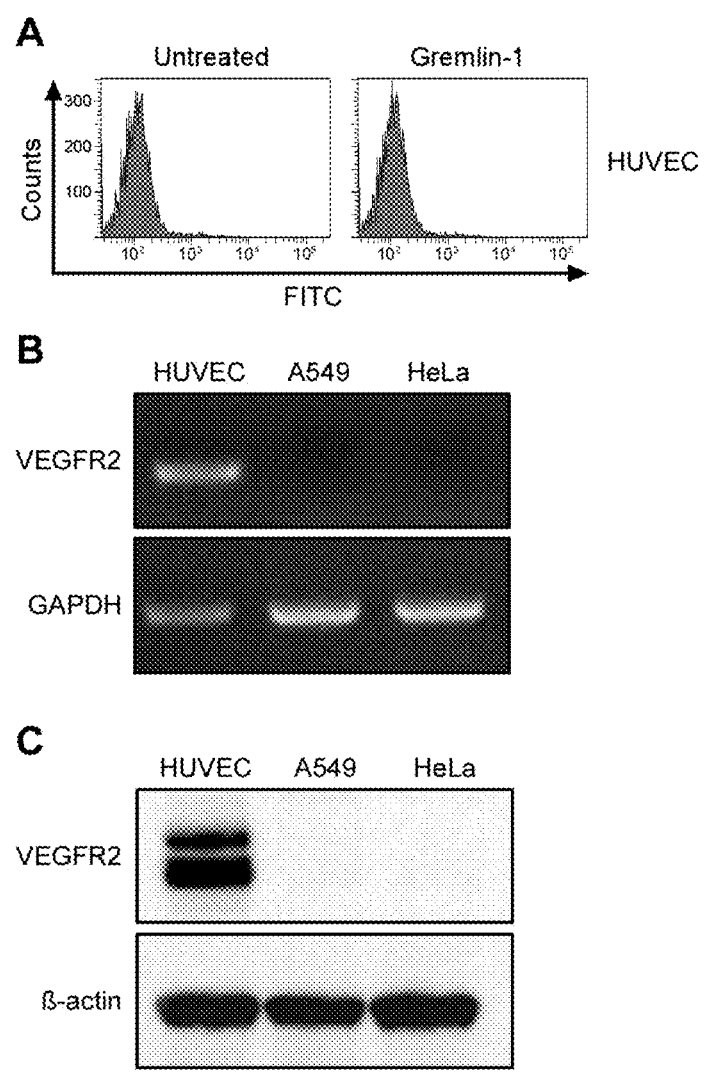
FIG. 2A is a graph showing the results obtained by treating HUVEC cells with gremlin-1, and then analyzing the cells by flow cytometry.
FIG. 2B shows the results obtained by treating HUVEC, A549 and HeLa cells with gremlin-1, and then measuring the expression of VEGFR2 mRNA and protein in the cells by RT-PCR.
FIG. 2C shows the results obtained by treating HUVEC, A549 and HeLa cells with gremlin-1, and then measuring the expression of VEGFR2 mRNA and protein in the cells by immunoblot analysis.

Whether gremlin-1 binds to HUVEC was analyzed by flow cytometry in the same manner as described in Example 3. The results of the analysis are shown in FIG. 2A. As can be seen therein, gremlin-1 did not bind to HUVEC. Because HUVEC expresses VEGFR2, the fact that gremlin-1 does not bind to HUVEC suggests that gremlin-1 binds to cancer cells in a VEGFR2-independent manner.

4-2: RT-PCR

The expression of VEGFR2 mRNA and protein in A549 cells, HeLa cells and HUVEC cells was measured by RT-PCR and immunoblot analysis.

Specifically, for RT-PCR, total RNA was isolated from A549 cells, HeLa cells and HUVEC cells using TRizol reagent (Invitrogen) according to the manufacturer's instructions. Then, cDNA was synthesized from the RNA using Superscript® III First-Strand synthesis system (Invitrogen). Using the following primers, RT-PCR was performed in 2720 Thermal Cycler (Applied Biosystems, Foster City, Calif.). The RT-PCR was performed for 35 cycles, each consisting of 94° C. for 30 sec, 56° C. for 30 sec and 72° C. for 1 min.

```
(1) VEGFR-2
F:
                                    (SEQ ID NO: 35)
5'-TGATCGGAAATGACACTGGA-3';
R:
                                    (SEQ ID NO: 36)
5'-TGCTTCACAGAAGACCATGC-3'

(2) Gremlin-1
F:
                                    (SEQ ID NO: 37)
5'-AACAGTCGCACCATCATCAA-3';
R:
                                    (SEQ ID NO: 38)
5'-AATTTCTTGGGCTTGCAGAA-3';

(3) GAPDH
F:
                                    (SEQ ID NO: 39)
5'-AGGTGAAGGTCGGAGTCAACG-3';
R:
                                    (SEQ ID NO: 40)
5'-AGGGGTCATTGATGGCAACA-3'.
```

The results of the RT-PCR are shown in FIG. 2B. As can be seen in FIG. 2B, VEGFR2 was present in HUVEC cells, but VEGFR2 was not detected in A549 and HeLa cells. Even though gremlin-1 interacted with cancer cells in Example 3, the fact that VEGFR2 mRNA was not detected indicates that the interaction between gremlin-1 and cancer cells is not mediated by VEGFR2.

4-3: Immunoblot Analysis

HUVEC, A549 cells and HeLa cells were lysed in ice-cold lysis buffer [50 mM Tris-HCl (pH 7.4), 150 mM NaCl, 2 mM EDTA, 1% Triton-X 100, 0.1% SDS, 1 mM PMSF] containing a protease inhibitor cocktail, and then Western blots were performed according to the procedure described in Lee M S et al., (2008) Hybridoma (Larchmt) 27: 18-24. Herein, VEGFR-2 (1:1,000 dilution; Cell Signaling Technology, Danvers, Mass.) and β-actin (1:10,000 dilution; Applied Biological Materials, Richmond, BC) were used as the primary antibodies, and horseradish peroxidase (HRP)-conjugated anti-mouse IgG (1:1,000 dilution; Pierce Chemical Co., Rockford, Ill.) or HRP-conjugated anti-rabbit IgG (1:1,000 dilution; Pierce Chemical Co.) was used as the secondary antibody. Blots were visualized using an enhanced chemiluminescence system (Pierce) according to the manufacturer's instructions.

The results of the immunoblot analysis are shown in FIG. 2C. As can be seen in FIG. 2C, A549 and HeLa cells did not expressed VEGFR2, unlike HUVEC. Such results also show that the interaction between gremlin-1 and cancer cells is not mediated by VEGFR2.

Example 5: Effect of BMP on Interaction of Gremlin-1 with Cancer Cells

Gremlin-1 is a BMP antagonist that binds specifically to BMP-2, BMP-4 and BMP-7 to inhibit their activities. BMPs are multifunctional growth factors that play an important role in the formation and homeostasis of many tissues. Also, BMP-2, BMP-4 and BMP-7 are frequently overexpressed in various cancers, including breast cancer and prostate cancer (Singh A et al., (2010) Cytokine Growth Factor Rev 21: 299-313; Chen D et al., (2004) Growth Factors 22: 233-241; Bobinac D et al., (2005) Croat Med J 46: 389-396). It was reported that BMP-4 reduces the proliferation of BCC cells and that the addition of gremlin-1 indirectly reduces the anti-proliferative effect of BMP-4 (Sneddon J B et al., (2006) Proc Natl Acad Sci USA 103: 14842-14847). Thus, whether BMP affects the interaction of gremlin-1 with cancer cells was examined.

5-1: Enzyme Immunoassay

Figure 3:
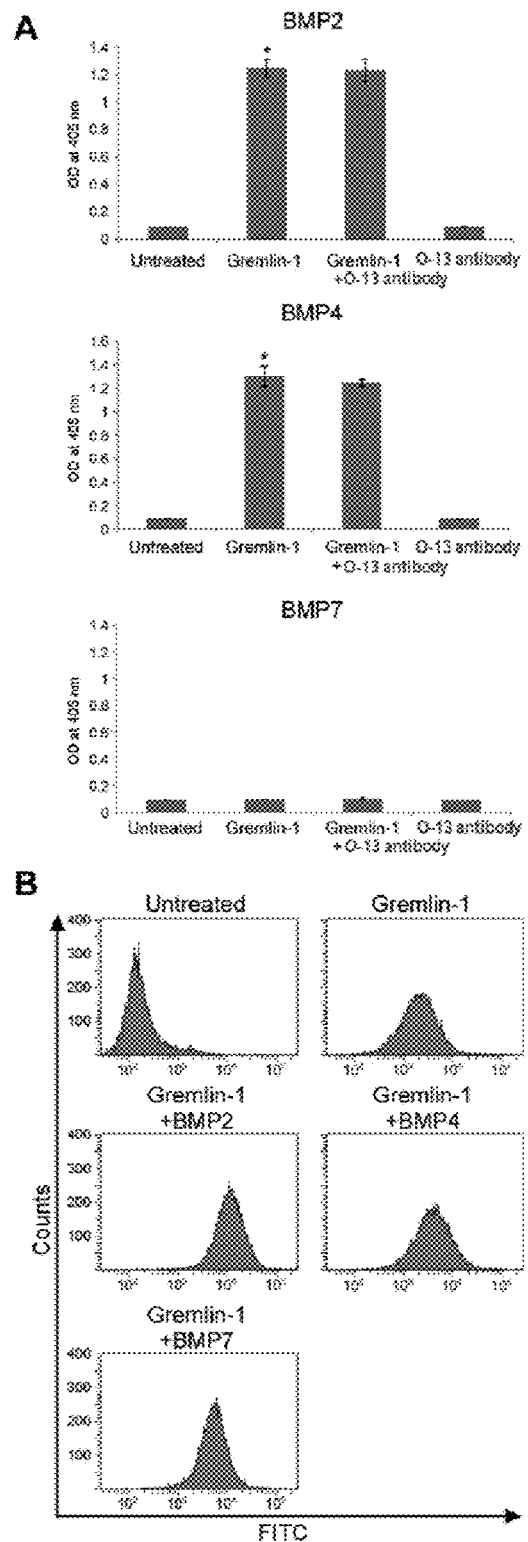
FIG. 3A shows the results obtained by allowing BMP2, BMP4 and BMP7 to interact with each of gremlin-1 alone, an antibody alone according to the present invention and a combination thereof, and then measuring the interaction of gremlin-1 with the BMPs by an enzyme immunoassay.
FIG. 3B is a graph showing the results obtained by treating A549 cells with gremlin-1, adding a 10 times molar excess of BMP-2, BMP-4 and BMP-7 thereto, and then analyzing the cells by flow cytometry.

In order to examine whether gremlin-1 binds to BMP, an enzyme immunoassay was performed in the following manner. Specifically, microtiter plates (Corning Costar Corp., Cambridge, Mass.) were coated with 100 nM of BMP-2, BMP-4, or BMP-7 (R&D Systems) and blocked with 1% (w/v) skim milk in PBS. Then, gremlin-1-Fc (10 nM) alone or gremlin-1-Fc (10 nM) plus 500 nM of the antibody (O-13) according to the present invention were added to each well. After washing, the plates were incubated with an HRP-conjugated IgG-Fc specific antibody (1:5,000 dilution; Pierce Chemical Co.). Then, 2,2'-azino-bis(3-ethylbenzothiazoline-6-sulphonic acid (ABTS) substrate solution (Amresco, Solon, Ohio) was used for the coloring reaction as described in Chung J et al., (2004) FASEB J 18: 361-363, and the absorbance at 405 nm was measured. The results of the measurement are shown in FIG. 3A. As can be seen in FIG. 3A, gremlin-1 interacted with BMP-2 and BMP-4, excluding BMP-7, and the antibody (O-13) according to the present invention did not affect the interaction of gremlin-1 with BMP-2 or BMP-4.

5-2: Flow Cytometry

A549 cells were treated with gremlin-1, and a 10 times molar excess of BMP-2, BMP-4 and BMP-7 were added thereto, followed by flow cytometry in the same manner as described in Example 3. The results are shown in FIG. 3B. As can be seen in FIG. 3B, the presence of BMP did not affect the interaction of gremlin-1 with A549 cells. These results indicate that there are two separate motifs in gremlin-1 that mediate its interaction with A549 cells and BMPs.

Example 6: Analysis of Effects of Gremlin-1 and its Antibody on Scattering and Migration of Cancer Cells 6-1: Cell Scattering Assay In order to examine the morphology of cancer cells treated with gremlin-1, A549 cells were analyzed by crystal violet staining assay. Specifically, A549 cells were seeded in 24-well plates ($1.0 \times 10^4$ cells/well) and treated with 100 nM of His-tagged gremlin-1 for 3 days. The medium was removed, and the cells were washed with PBS and fixed with 4% paraformaldehyde in PBS for 10 min. The cells were stained with 0.05% crystal violet in distilled water for 30 min. The staining solution was removed and the cells were washed 3 times with PBS according to the method described in Li X L et al., (2009) Cancer Chemother Pharmacol 64: 1097-1104. Images were obtained using a Leica DFL290 camera (Leica Microsystems, Wetzlar, Germany) and analyzed using Leica application suite software (Leica Microsystems).

Figure 4:
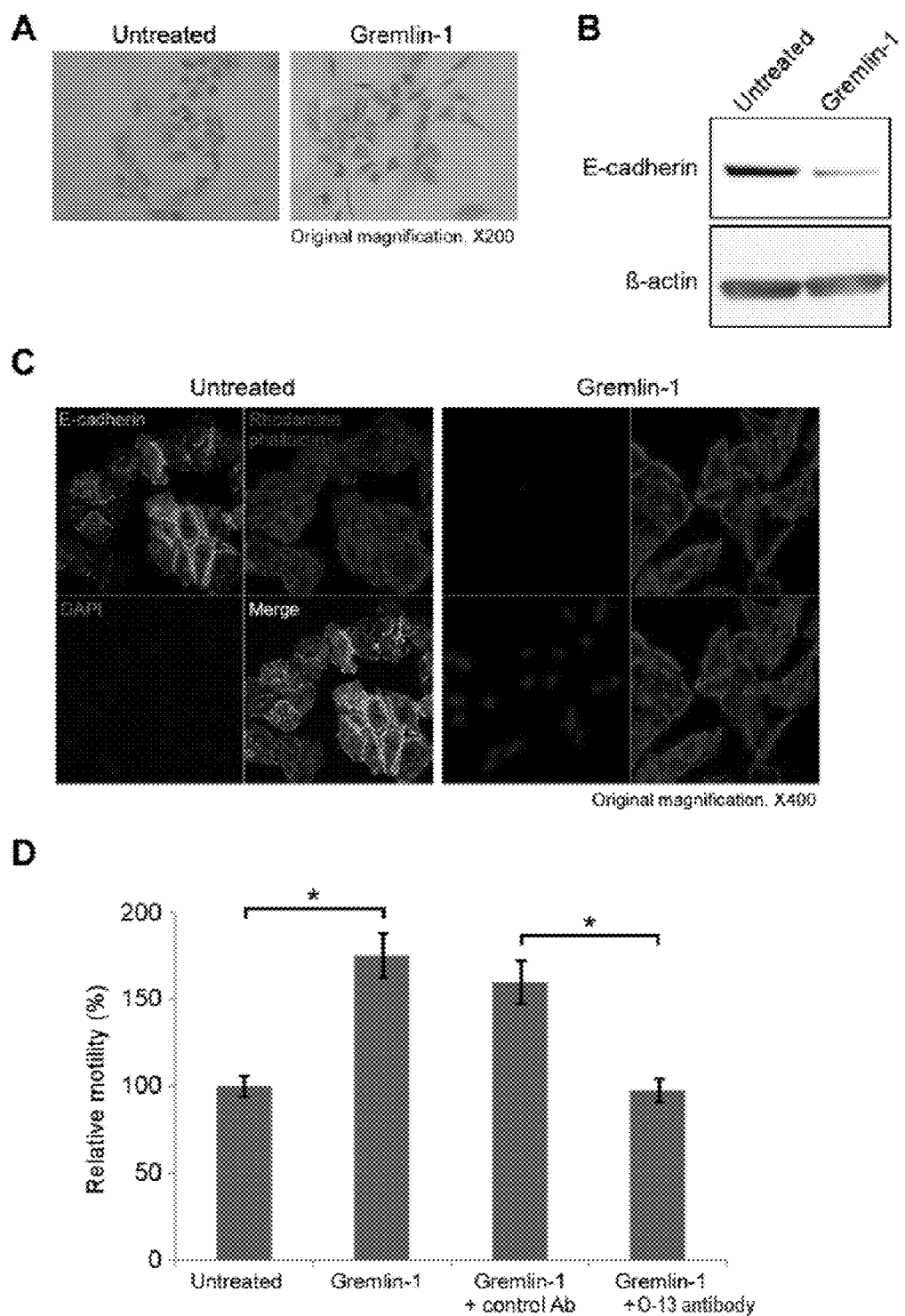
FIG. 4A is an image of A549 cells stained with crystal violet after treatment with gremlin-1.
FIG. 4B shows the results obtained by treating A549 cells with gremlin-1, and then measuring the expression of E-cadherin in the cells by immunoblot analysis.
FIG. 4C shows the results obtained by treating A549 cells with gremlin-1, and then measuring the expression of E-cadherin in the cells by immunofluorescence staining.
FIG. 4D is a graph showing the results obtained by treating A549 cells with each of gremlin-1 alone, and a combination of gremlin-1 with an antibody according to the present invention or a control antibody, and then measuring the migration of the cells.

The obtained images are shown in FIG. 4A. As can be seen in FIG. 4A, the morphology of A549 cells treated with gremlin-1 was similar to that of fibroblasts, the cells became scattered.

6-2: Analysis of Change in Expression of E-Cadherin

Down-regulation of E-cadherin is associated with epithelial-mesenchymal transition (EMT), and the inhibition of E-cadherin and EMT is observed in cancer development (Perl A K et al., (1998) Nature 392: 190-193). Thus, the change in expression of E-cadherin caused by treatment with gremlin-1 was examined by immunoblot analysis and immunofluorescence staining.

For immunoblot analysis, A549 cells ($1.0 \times 10^5$ cells/well) were seeded onto a 60-mm dish and grown to 50% confluence. The cells were treated with 100 nM of His-tagged gremlin-1 for 3 days. The cells were lysed in a cold lysis buffer [50 mM Tris-HCl (pH 7.4), 150 mM NaCl, 2 mM EDTA, 1% Triton-X 100, 0.1% SDS, 1 mM PMSF] containing a protease inhibitor cocktail (Sigma-Aldrich, St. Louis, Mo.), and was then analyzed by Western blotting according to the method described in Lee M S et al., (2008) Hybridoma (Larchmt) 27: 18-24. Herein, E-cadherin (1:1,000 dilution; Abcam) and β-actin (1:10,000 dilution; Applied Biological Materials, Richmond, BC) antibodies were used as the primary antibodies, and horseradish peroxidase (HRP)-conjugated anti-mouse IgG (1:1,000 dilution; Pierce Chemical Co., Rockford, Ill.) or HRP-conjugated anti-rabbit IgG (1:1,000 dilution; Pierce Chemical Co.) was used as the secondary antibody. The blots were visualized using an enhanced chemiluminescence system (Pierce) according to the manufacturer's instructions.

The results are shown in FIG. 4B. As can be seen in FIG. 4B, the expression of E-cadherin in A549 cells treated with gremlin-1 significantly decreased.

For immunofluorescence staining, A549 cells ($1.0 \times 10^5$ cells/well) were seeded on glass coverslips coated with poly-L-lysine (100 μg/ml, Sigma) and were grown to 50% confluence. The cells were treated with 100 nM of His-tagged gremlin-1 for 3 days, rinsed in PBS, and fixed in 4% paraformaldehyde in PBS for 30 min at room temperature. The fixed cells were permeabilized with 0.2% Triton X-100 in PBS (PBST) at room temperature for 10 min, and then blocked with 1% gelatin in PBST for 30 min at room temperature. Immunofluorescent staining was performed using an E-cadherin antibody (Abcam) followed by an Alexa 488-conjugated secondary antibody (Invitrogen). Nuclei were stained with DAPI (1:1,000 dilution; Invitrogen), and actin filaments were stained using rhodamine-phalloidin (1:1,000 dilution; Invitrogen). Coverslips were mounted on glass slides using aqueous mounting medium with anti-fading agents (Biomeda Corp., Foster City, Calif.). Then, images were acquired using a LSM 5 PASCAL Laser Scanning Microscope (Carl Zeiss, Germany) and analyzed using LSM 5 PASCAL software.

The results are shown in FIG. 4C. As can be seen in FIG. 4C, the expression of E-cadherin in A549 cells treated with gremlin-1 significantly decreased.

6-3: Cell Migration Assay

In order to examine whether cells migrate, a cell migration assay was performed in the following manner. Specifically, cells were seeded in 24-well plates at a density of $1.0 \times 10^5$ cells per well. A scratch wound was generated by scratching with a pipette tip. After rinsing with media to remove detached cells, 100 nM of His-tagged gremlin-1 was added to the cultures for 24 hours. Images were taken from each well immediately and again after 24 hours using a Leica DFL290 camera (Leica Microsystems). The distance that cells migrated through the area created by scratching was determined by measuring the wound width at 24 hours and subtracting it from the wound width at the start. The values obtained were then expressed as % migration, setting the migrating distance of cells untreated as 100%.

To determine the neutralizing efficacy of the antibody (O-13) according to the present invention, scratched cells were incubated for 24 hours with His-tagged gremlin-1 alone or plus 10 μM antibody (O-13) according to the present invention (or 10 μM control antibody). The distance was determined as described above.

Using the same protocol, mock-transfected A549 cells and gremlin-1-transfected A549 cells were seeded and scratched. Mock-A549 cells were cultured without any treatment while gremlin-1-A549 cells were cultured for 24 hours in the presence of 10 μM antibody (O-13) according to the present invention or control antibody. The distance was determined as described above. The results were representative of three independent experiments.

The results of the measurement are shown in FIG. 4D. As can be seen in FIG. 4D, treatment with gremlin-1 significantly increased the migration of A549 cells, and this effect was completely abolished upon addition of the neutralizing antibody.

These results indicate that gremlin-1 induces the scattering and migration of cancer cells and that this scattering and migration can be inhibited using the gremlin-1 antibody.

Example 7: Characterization of A6549 Cells Transfected with Gremlin-1

7-1: Measurement of Expression Levels of Gremlin-1 mRNA and Protein

For the gremlin-1 A549 cell line and mock-A549 cell line constructed in Example 1-2, changes in the expression levels of gremlin-1 mRNA and protein were analyzed by RT-PCR and Western blotting as described above.

Figure 5:
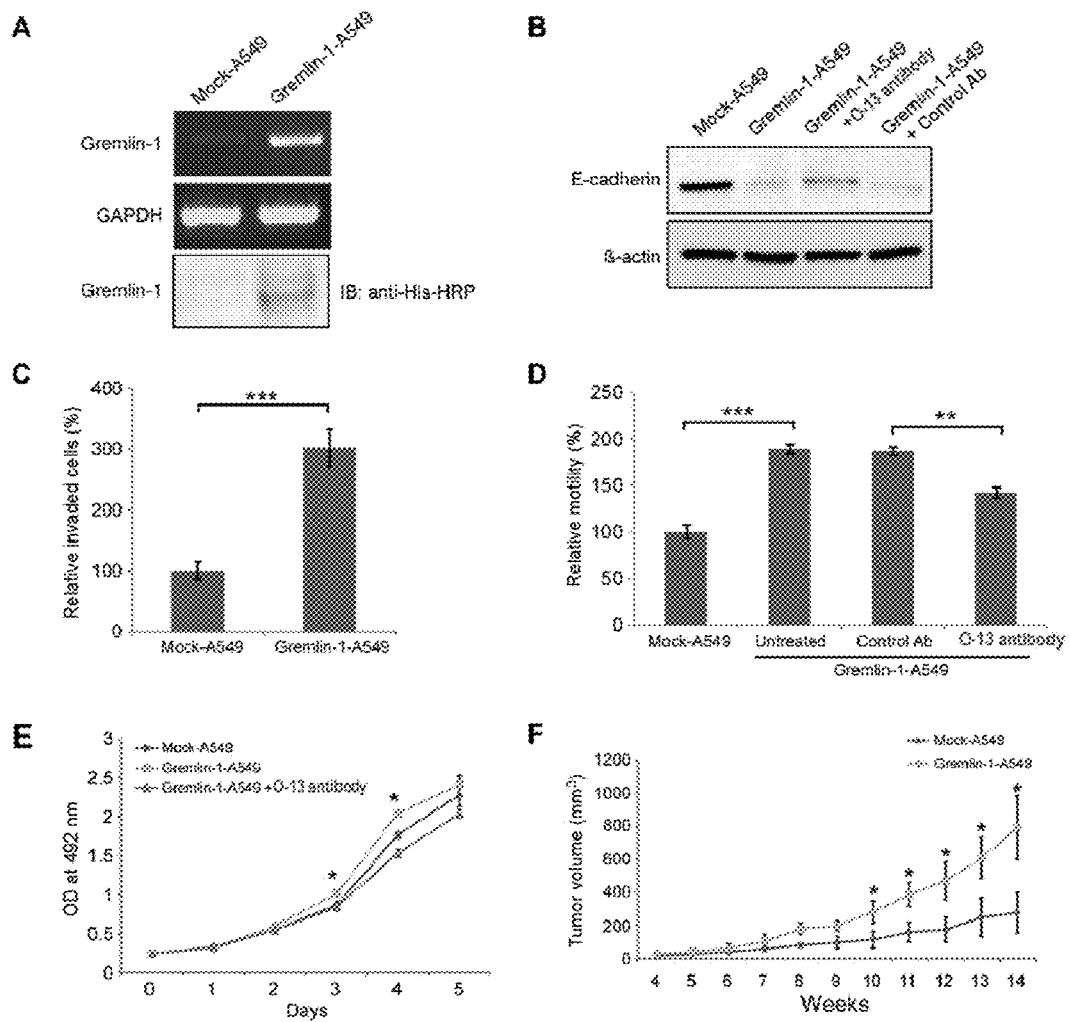
FIG. 5A shows the results of measuring the expression of gremlin-1 mRNA and protein in a gremlin-1-A549 cell line and a mock-A549 cell line by RT-PCR and Western blot analysis.
FIG. 5B shows the results of measuring the expression levels of E-cadherin in a gremlin-1-A549 cell line, a mock-A549 cell line, and a gremlin-1-A549 cell line treated with an antibody according to the present invention or a control antibody, by immunoblot analysis.
FIG. 5C is a graph showing the number of invaded cells in a mock-A549 cell line and a gremlin-1-A549 cells.
FIG. 5D is a graph showing the migration of cells in a gremlin-1-A549 cell line, a mock-A549 cell line, and a gremlin-1-A549 cell line treated with an antibody according to the present invention or a control antibody.
FIG. 5E is a graph showing the results of measuring the cell growth of each of a gremlin-1-A549 cell line, a mock-A549 cell line, and a gremlin-1-A549 cell line treated with an antibody according to the present invention.
FIG. 5F is a graph showing the results of measuring the volume of tumors formed after injecting nude mice with each of a gremlin-1-A549 cell line and a mock-A549 cell line.
Figure 6A:
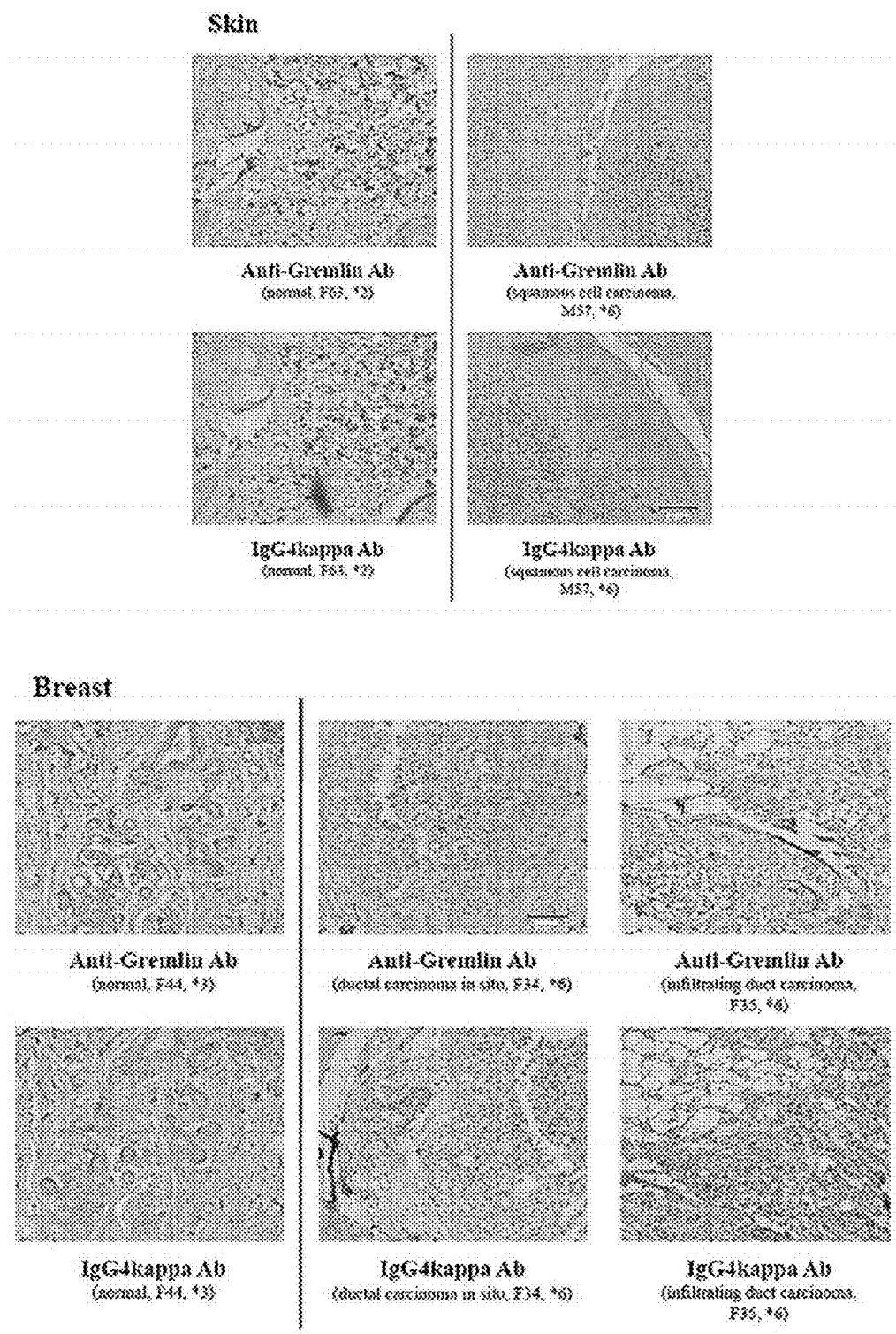
FIGS. 6A to 6I show the results obtained by treating normal tissues and cancer tissues (cancer tissues of skin, breast, lymph node, lung, liver, esophagus, stomach, colon, rectum, kidney, urinary bladder, prostate, testis, uterine cervix, endometrium and thyroid) with an antibody (O-13) according to the present invention, and measuring the expression level of gremlin-1 in the tissues by immunohistochemical staining.
Figure 6B:
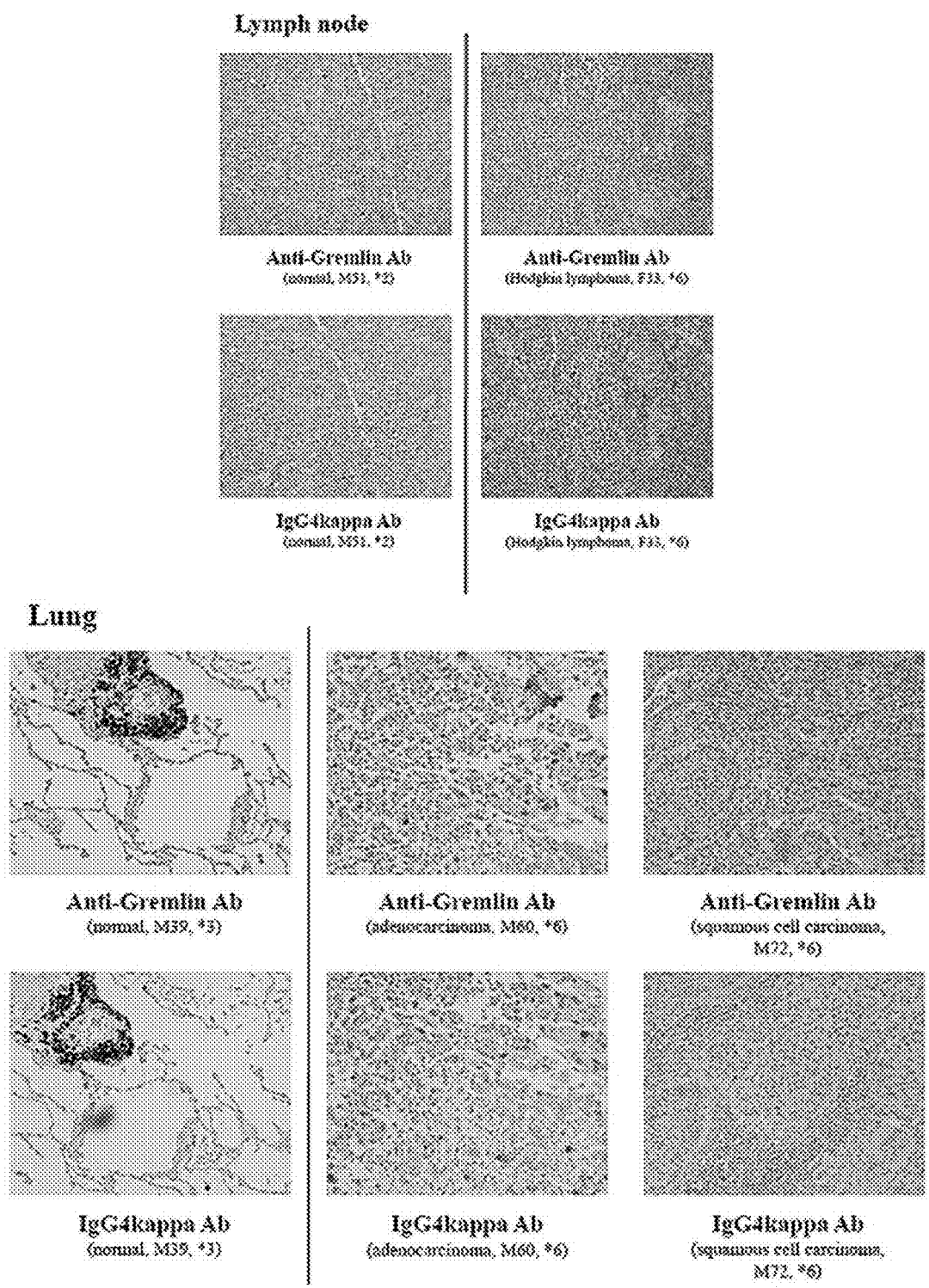
Figure 6C:
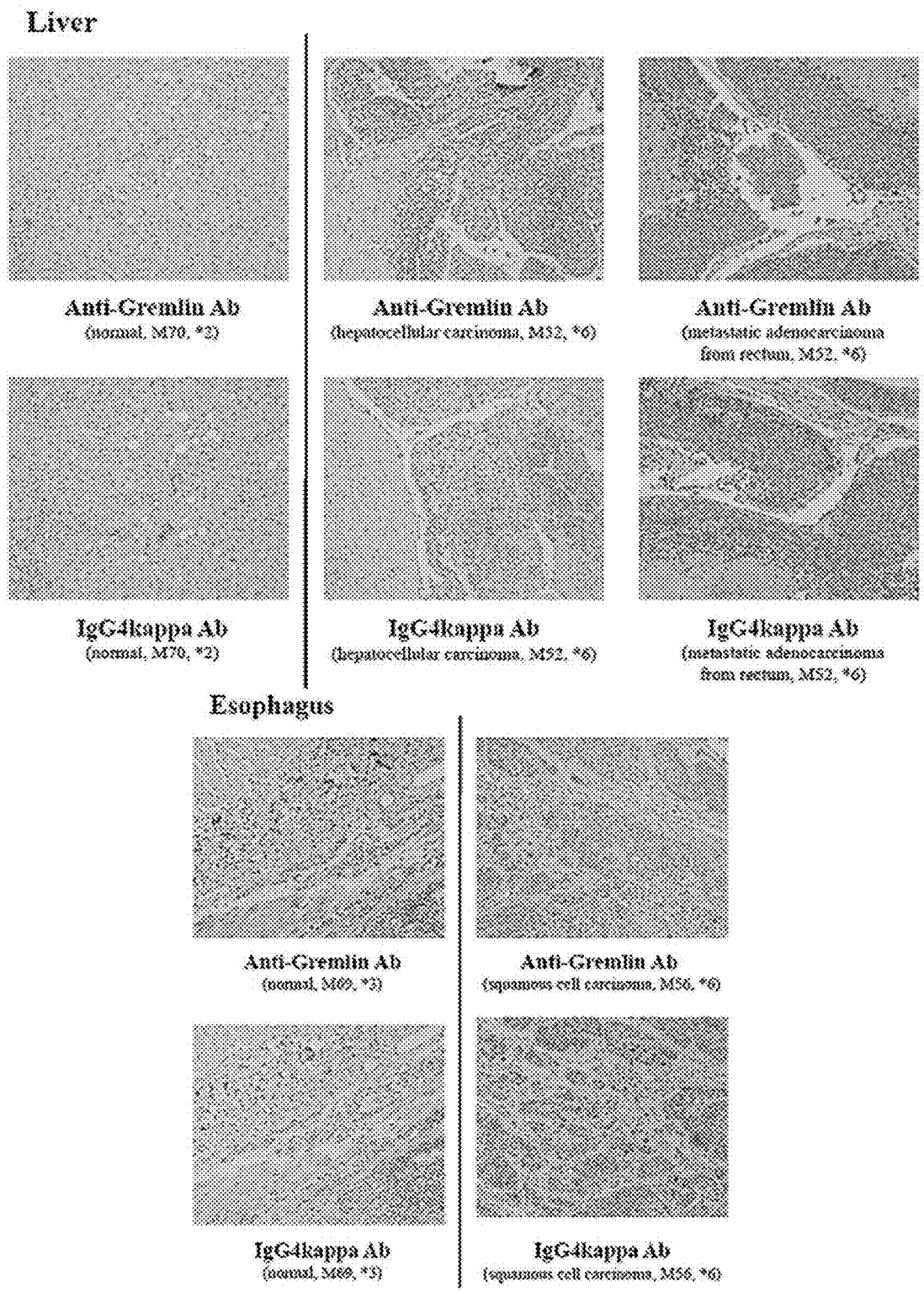
Figure 6D:
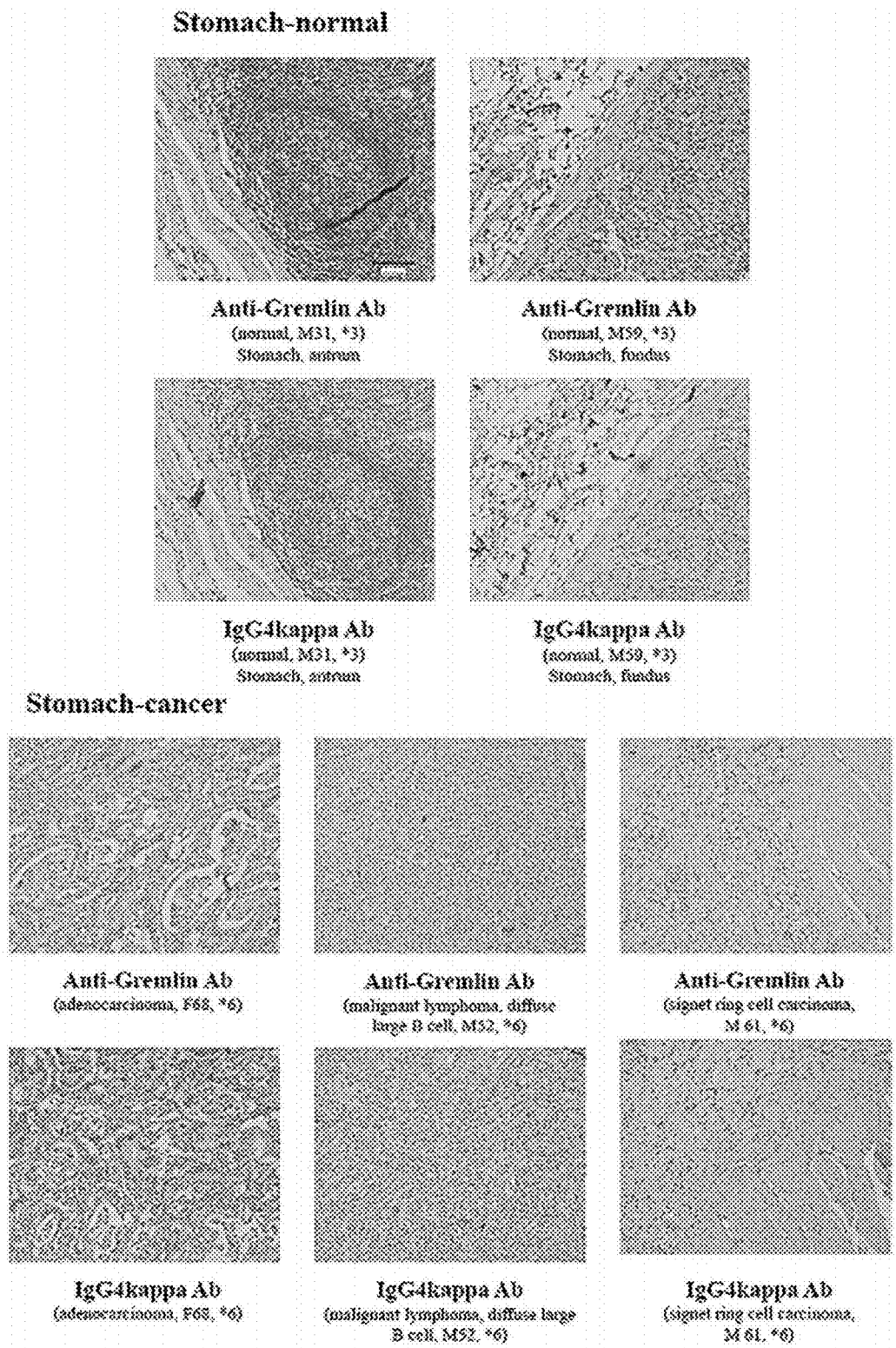
Figure 6E:
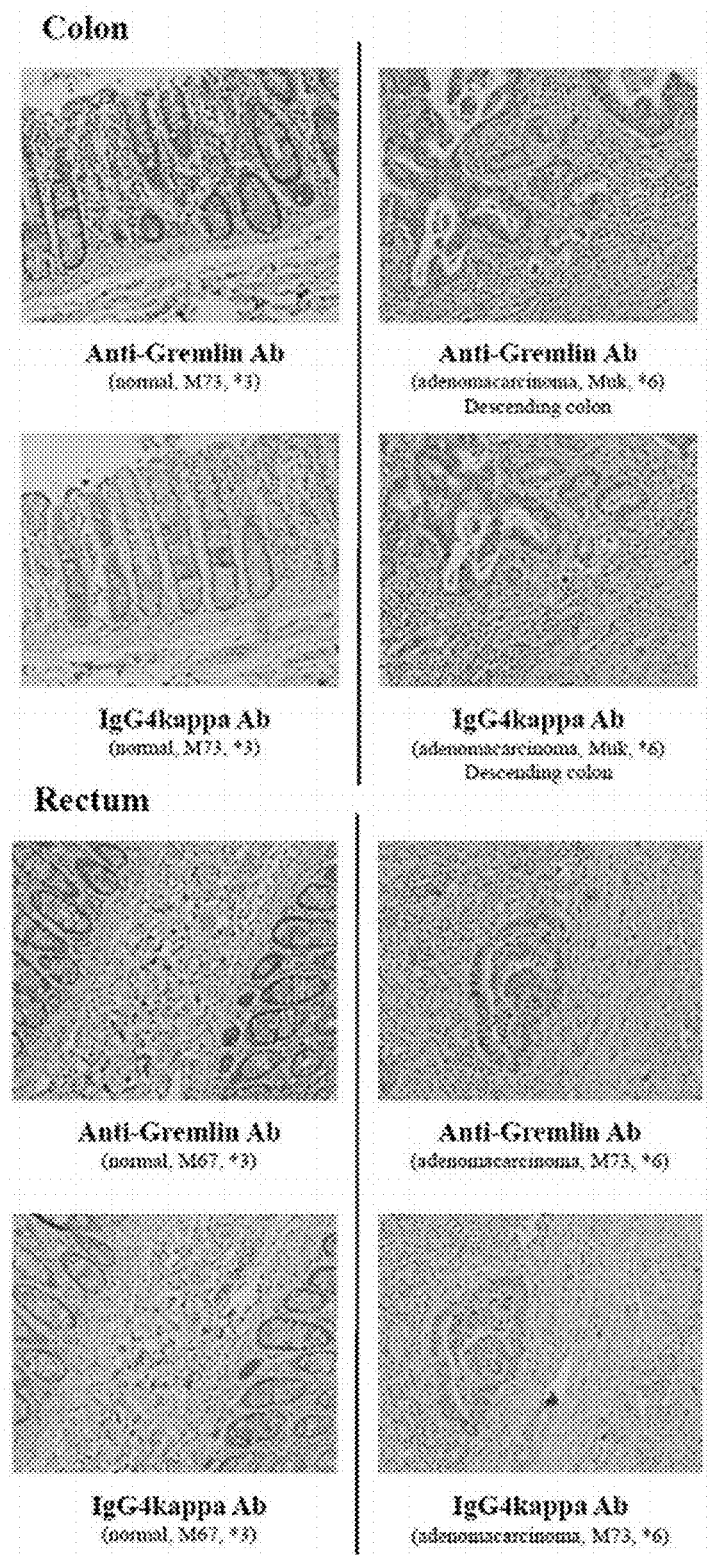
Figure 6F:
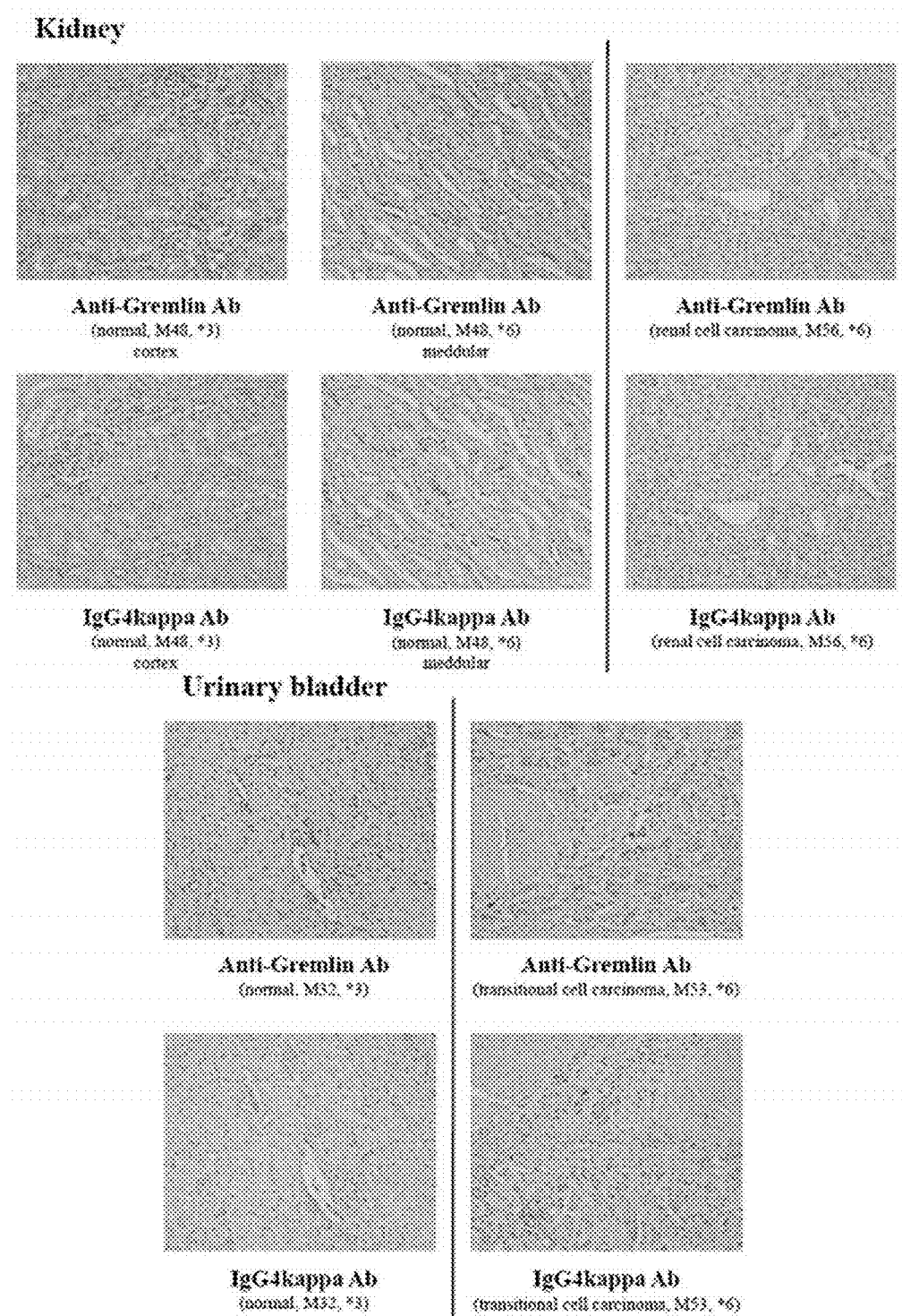
Figure 6G:
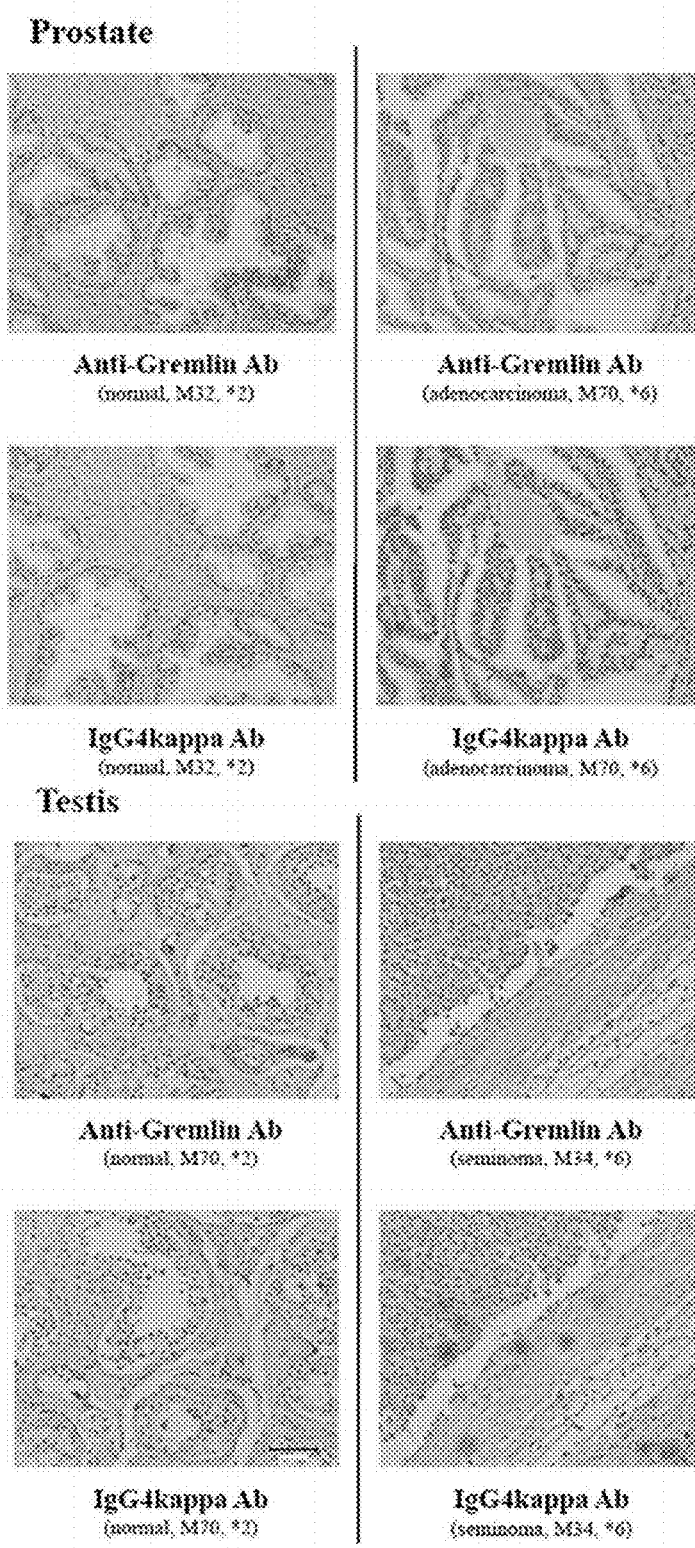
Figure 6H:
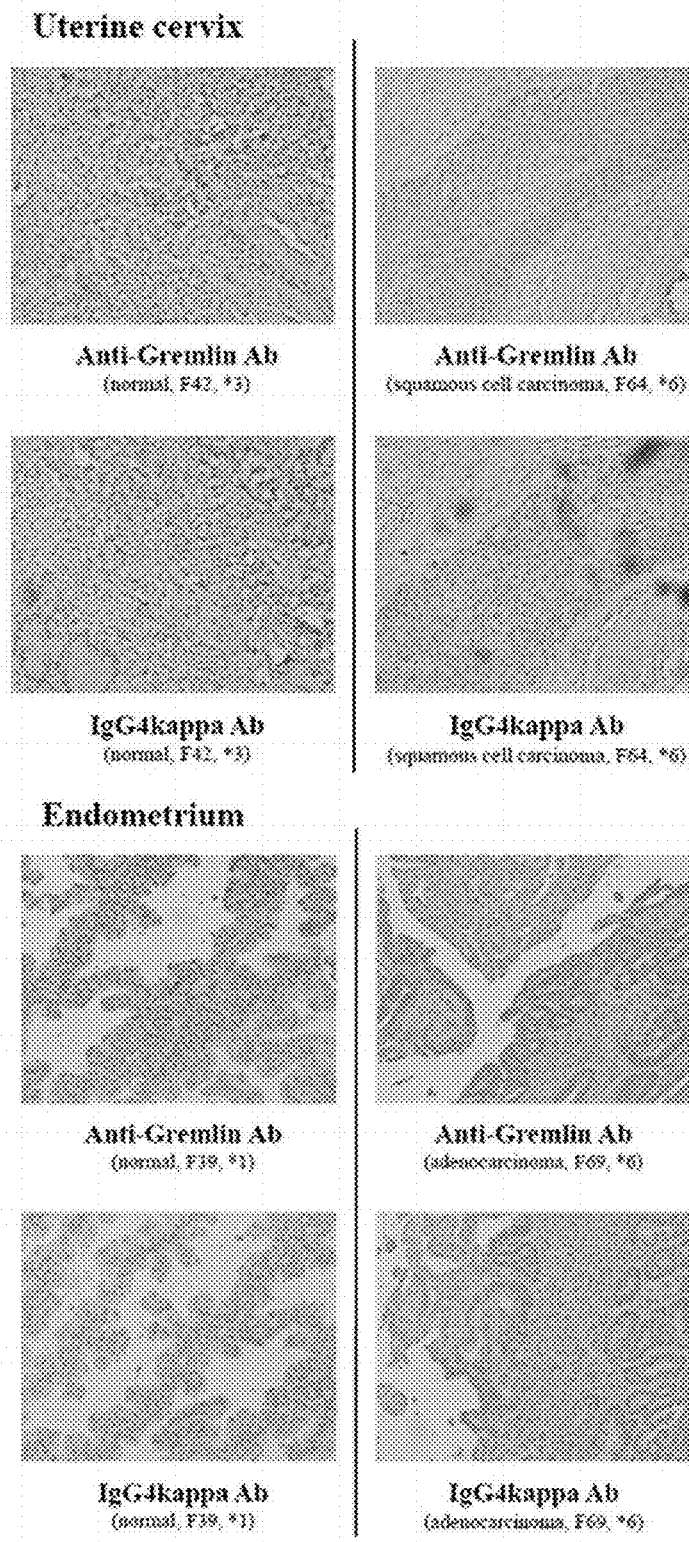
Figure 6I:
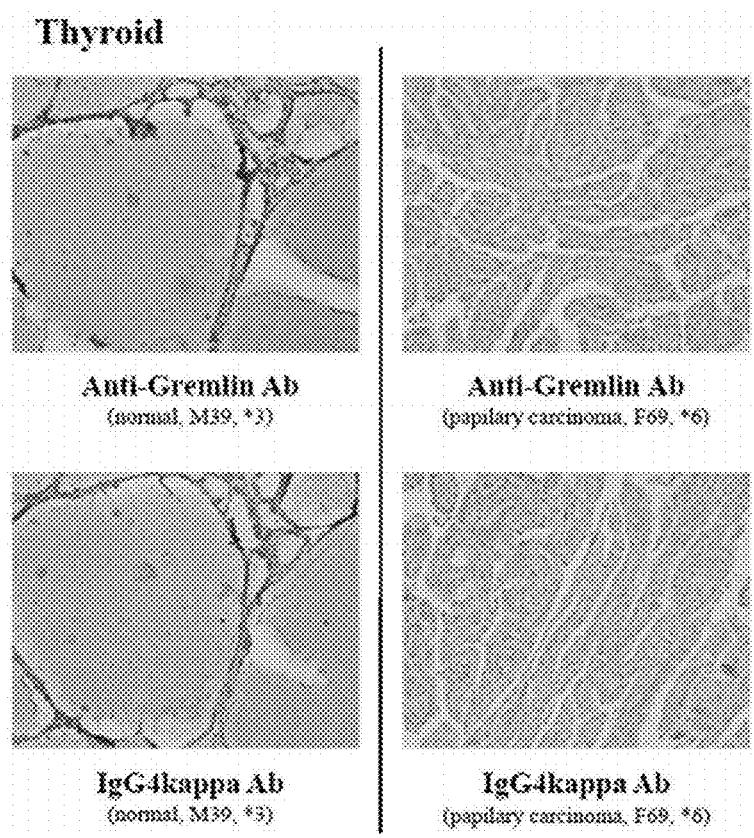

The results of the analysis are shown in FIG. 5A. As can be seen in FIG. 5A, gremlin-1 mRNA and protein were not expressed in the mock-A549 cell line, whereas the expression levels thereof significantly increased in the gremlin-1-A549 cell line.

7-2: Measurement of Expression Level of E-Cadherin

In addition, the expression level of E-cadherin was measured according to the immunoblot analysis method as follows. Specifically, gremlin-1-A549 cells and mock-A549 cells ($1.0 \times 10^5$ cells/well) were seeded on 60-mm dishes and grown to 50% confluence. The mock-A549 cells were cultured without any treatment, and the gremlin-1-A549 cells were cultured in the presence of 10 μM antibody (O-13) according to the present invention or control antibody (Palivizumab, Synagis, Abbott Laboratories, Abbott Park, Ill.) for 24 hours. The cells were lysed and analyzed according to the immunoblot analysis method described in Example 6.

The results of the analysis are shown in FIG. 5B. As can be seen in FIG. 5B, the expression of E-cadherin decreased in the gremlin1-A549 cells compared to the mock-A549 cells, and slightly increased upon addition of the neutralizing antibody.

7-3: Cell Invasion Assay

Cell invasion assays were performed using ECM-coated inner chambers (Chemicon, Temecula, Calif.) according to the manufacturer's instructions. Mock-A549 cells and gremlin-1-A549 cells (3.0×10⁵ cells per well) were suspended in 300 μL of serum-free media. Complete media (500 μL) containing 10% FBS was added to the bottom wells of the plate. The cells were incubated for 48 hours. Non-migrating cells were wiped away and washed with PBS. The membranes were fixed with 4% paraformaldehyde in PBS and stained with a crystal violet stain solution (Chemicon). Images were acquired using a Leica DFL290 camera (Leica Microsystems) and analyzed using Leica application suite software. Migrated cells were counted in four separated fields per well. The values obtained were then expressed as % invasion, setting the cell counts of mock-A549 cells as 100%.

The results are shown in FIG. 5C. As can be seen in FIG. 5C, a larger number of gremlin-1-A549 cells migrated as compared to mock-A549 cells.

7-4: Cell Migration Assay

A cell migration assay was performed according to the method described in Example 6. Mock-A549 cells and gremlin-1-A549 cells were plated and scratched. The mock-A549 cells were incubated without any treatment, and the gremlin-1-A549 cells were incubated in the presence of 10 μM antibody (O-13) according to the present invention or control antibody for 24 hours. The distance was determined as described above.

The results of the measurement are shown in FIG. 5D. As can be seen in FIG. 5D, the gremlin-1-A549 cells showed increased migration compared to the mock-A549 cells, and this increased migration was significantly inhibited upon addition of the antibody (O-13) according to the present invention.

7-5: Cell Proliferation Assay

In order to examine whether gremlin-1 affects cell growth, a cell proliferation assay was performed using CellTiter 96 Aqueous One Solution Cell Proliferation Assay (Promega, Madison, Wis.) in 10% FBS-containing RPMI-1640 media in 96-well plates. Specifically, mock-A549 cells and gremlin-1-A549 cells were seeded at a density of 1,000 cells per well. After 24 hours, the cells were washed twice with serum-free medium and cultured in 100 μL of complete medium with or without 3 μM of the antibody (O-13) according to the present invention. Cell proliferation was determined by using Labsystems Multiskan Ascent Photometric plate reader (Thermo Labsystems, Franklin, Mass.) for a 96 well plate with a 492 nm filter. Experiments were performed in triplicate.

The results of the measurement are shown in FIG. 5E. As can be seen in FIG. 5E, the gremlin-1-A549 cells showed a higher growth rate compared to the mock-A549 cells, and the increased growth rate was inhibited by the addition of the antibody (O-13) according to the present invention.

7-6: Tumor Growth Assay

In order to evaluate the effect of gremlin-1 on tumorigenesis, gremlin-1-A549 cells or mock-A549 cells were injected subcutaneously into nude mice as described below, and then tumor volumes were measured.

All animal experiments were authorized by the Institute of Laboratory Animal Resources Seoul National University and Use Committee (Permit number: SNU-11-0207). Gremlin-1-A549 cells and mock-A549 cells (1.0×10⁶ cells/mouse) subcutaneously in the right flank of 4- to 6 week-old female, athymic nude mice (7 mice in each treatment group). Tumor formation and size were assessed weekly by caliper measurements of the length and width of the tumors. Tumor volumes were calculated using the following formula (Tomayko M M et al., (1989) Cancer Chemother Pharmacol 24: 148-154):

$$\text{Tumor volume}=(\text{length}\times\text{width}\times\text{height})/2$$

The results of the measurement are shown in FIG. 5F. As can be seen therein, the tumor volume in mice injected with gremlin-1-A549 cells increased more rapidly than those injected with mock-A549 cells, with an approximately 500 mm³ difference in tumor volume at 14 weeks post injection. This result suggests that increased expression of gremlin-1 may play a important role in tumorigenesis.

Example 8: Diagnosis of Cancer Using Gremlin-1 Antibody

Normal tissues and cancer tissues (cancer tissues of skin, breast, lymph node, lung, liver, esophagus, stomach, colon, rectum, kidney, urinary bladder, prostate, testis, uterine cervix, endometrium and thyroid) were treated with the antibody (O-13) according to the present invention, and the expression levels of gremlin-1 in the tissues were measured by immunohistochemical staining.

Specifically, 0.5 ml of the antibody (O-13) (2 mg/ml) according to the present invention was mixed with FITC reagent to label the antibody with FITC according to the manufacturer's instructions (Pierce FITC antibody labeling kit, 53027). Tissue array slides (Superbiochip BC8) immobilized with normal tissues and cancer tissues were deparaffinized according to the manufacturer's instructions. The slides were placed in a glass jar containing an antigen retrieval solution (TE pH 9.0), and then heated in a pressure cooker for 30 minutes. The slides were taken out of the jar, cooled to 60~65° C., washed with distilled water, immersed in 95% cold ethanol for 10 minutes, and then washed with running water for 10 minutes. Next, the slides were treated with the FITC-labeled antibody using Thermo Ultra-vision LP detection system (Thermo) according to the manufacturer's instructions. The antibody was used at 1:75, and anti-FITC mouse IgG (LS bio) was used at 1:200. Thereafter, the slides were treated with a HRP-conjugated polymer (Labvision) for 15 minutes, and then treated with DAB solution for 1 minute. The slides were counter-stained with Mayer's hematoxylin solution, and then observed with a microscope in the order of 4×, 200× and 400× magnifications. In the experiment, IgG kappa antibody was used as a control.

The results of the experiment are shown in FIGS. 6A to 6I. As can be seen in FIG. 6, the antibody of the present invention showed strong reactivity in skin, breast, lymph node, lung, liver, esophagus, stomach, colon, rectum, kidney, urinary bladder, prostate, testis, uterine cervix, endometrium and thyroid cancer tissues as compared to that in normal tissues. This indicates that gremlin-1 is distributed and overexpressed in various cancer tissues. Thus, it is expected that cancer or immune disease can be diagnosed using the gremlin-1 antibody of the present invention.

The invention claimed is:

1. An anti-gremlin-1 antibody, comprising a light-chain variable region and a heavy-chain variable region selected from the group consisting of those having the following amino acid sequences, respectively:
   a light-chain variable region comprising amino acids 23-35 of CDR1, amino acids 51-57 of CDR2, and amino acids 90-100 of CDR3 in an amino acid sequence of SEQ ID NO: 5 and a heavy-chain variable region comprising amino acids 26-35 of CDR1, amino acids 50-66 of CDR2, and amino acids 99-110 of CDR3 in an amino acid sequence of SEQ ID NO: 6;
   a light-chain variable region comprising amino acids 23-35 of CDR1, amino acids 51-57 of CDR2, and amino acids 90-100 of CDR3 in an amino acid sequence of SEQ ID NO: 7 and a heavy-chain variable region comprising amino acids 26-35 of CDR1, amino acids 50-66 of CDR2, and amino acids 99-110 of CDR3 in an amino acid sequence of SEQ ID NO: 8; and
   a light-chain variable region comprising amino acids 23-35 of CDR1, amino acids 51-57 of CDR2, and amino acids 90-100 of CDR3 in an amino acid sequence of SEQ ID NO: 9 and a heavy-chain variable region comprising amino acids 26-35 of CDR1, amino acids 50-66 of CDR2, and amino acids 90-110 of CDR3 in an amino acid sequence of SEQ ID NO: 10.

2. The anti-gremlin-1 antibody of claim 1, wherein the antibody comprises a light-chain constant region, a heavy-chain constant region, a light-chain variable region and a heavy-chain variable region, in which the light chain variable region and the heavy chain variable region are selected from the group consisting of those having the following amino acid sequences, respectively:
   a light-chain variable region having an amino acid sequence of SEQ ID NO: 5 and a heavy-chain variable region having an amino acid sequence of SEQ ID NO: 6;

a light-chain variable region having an amino acid sequence of SEQ ID NO: 7 and a heavy-chain variable region having an amino acid sequence of SEQ ID NO: 8;

a light-chain variable region having an amino acid sequence of SEQ ID NO: 9 and a heavy-chain variable region having an amino acid sequence of SEQ ID NO: 10;

a light-chain variable region having an amino acid sequence of SEQ ID NO: 13 and a heavy-chain variable region having an amino acid sequence of SEQ ID NO: 14.

3. The anti-gremlin-1 antibody of claim 2, wherein the light-chain constant region and heavy-chain constant region of the antibody are of human or rabbit origin.

4. A pharmaceutical composition, comprising the antibody of claim 1 and a pharmaceutically acceptable carrier.

5. A kit for diagnosing cancer, comprising the antibody of claim 1.

* * * * *